PATENT

US005879938A

United States Patent [19]
Usman et al.

[11] Patent Number: 5,879,938
[45] Date of Patent: *Mar. 9, 1999

[54] BASE-MODIFIED ENZYMATIC NUCLEIC ACID

[75] Inventors: Nassim Usman, Boulder; Leonid Beigelman, Longmont; James McSwiggen; Alex Karpeisky, both of Boulder, all of Colo.

[73] Assignee: Ribozyme Pharmaceuticals, Inc., Boulder, Colo.

[ * ] Notice: The term of this patent shall not extend beyond the expiration date of Pat. No. 5,672,501.

[21] Appl. No.: 435,398

[22] Filed: May 5, 1995

Related U.S. Application Data

[60] Division of Ser. No. 363,254, Dec. 23, 1994, which is a continuation-in-part of Ser. No. 963,322, Oct. 15, 1992, abandoned, and Ser. No. 149,210, Nov. 8, 1993.

[51] Int. Cl.⁶ .......................... C07H 21/04; C12N 15/00; C12N 15/85
[52] U.S. Cl. ........................ 435/325; 435/6; 435/91.1; 435/91.31; 435/172.3; 435/366; 536/23.1; 536/24.1; 536/24.5
[58] Field of Search ................. 536/24.5, 23.1, 536/24.1; 435/91.31, 6, 91.1, 172.3, 325, 366

[56] References Cited

U.S. PATENT DOCUMENTS

| | | | |
|---|---|---|---|
| 4,987,071 | 1/1991 | Cech et al. | 435/91.31 |
| 5,298,612 | 3/1994 | Jennings et al. | 536/23.2 |
| 5,334,711 | 8/1994 | Sproat et al. | 536/24.5 |

FOREIGN PATENT DOCUMENTS

| | | |
|---|---|---|
| 0360257 | 3/1990 | European Pat. Off. . |
| 0519463 | 12/1992 | European Pat. Off. . |
| 0558944 | 9/1993 | European Pat. Off. . |
| 9104319 | 9/1990 | WIPO . |
| 9103162 | 3/1991 | WIPO . |
| 9110674 | 7/1991 | WIPO . |
| 9201786 | 2/1992 | WIPO . |
| 9203566 | 3/1992 | WIPO . |
| 9206693 | 4/1992 | WIPO . |
| 9207065 | 4/1992 | WIPO . |
| 9315187 | 8/1993 | WIPO . |
| 9323569 | 11/1993 | WIPO . |
| 9402595 | 2/1994 | WIPO . |

OTHER PUBLICATIONS

Adams et al., "A Convenient Synthesis of S–Cyanoethyl––Protected 4–Thiouridine and its Incorporation into Oligoribonucleotides," *Tetrahedron Letters* 35:765–768 (1994).

Bevilacqua and Turner, "Comparision of Binding of Mixed Ribose–Deoxyribose Analogues of CUCU to a Ribozyme and to GGAGAA by Equilibrium Dialysis: Evidence for Ribozyme Specific Interactions with 2' OH Groups," *Biochemistry* 30:10632–10690 (1991).

Chowrira and Burke, "Binding and Cleavage of Nucleic Acids by the 'Hairpin' Ribozyme," *Biochemistry* 30:8518–8522 (1991).

Collins and Olive, "Reaction Conditions and Kinetics of Self–Cleavage of a Ribozyme Derived From Neurospora VS RNA," *Biochemistry* 32:2795–2799 (1993).

Fu et al., "Importance of Specific Guanosine $N^7$–Nitrogens and Purine Amino Groups for Efficient Cleavage by a Hammerhead Riobzyme," *Biochemistry* 32:10629–10637 (1993).

Fu and Mclaughlin, "Importance of Specific Adenosine $N^7$ Nitrogens for Efficient Cleavage by a Hammerhead Ribozyme. A Model for Magnesium Binding," *Biochemistry* 31:10941–10949 (1992).

Fu and McLaughlin, "Importance of Specific Purine Amino and Hydroxyl Groups For Efficient Cleavage by a Hammerhead Ribozyme," *Proc. Natl. Acad. Sci. USA* 89:3985–3989 (1992).

Grasby et al., "The synthesis of oligoribonucleotides containing $O^6$–methylguanosine: the role of conserved guanosine residues in hammerhead riboozyme cleavage," *Nucleic Acids Research* 21:4444–4450 (1993).

Guerrier–Takada et al., "The RNA Moiety of Ribonuclease P Is the Catalytic Subunit of the Enzyme," *Cell* 35:849–857 (1983).

Hampel et al., "'Hairpin' Catalytic RNA Model: Evidence for Helices and Sequence Requirement for Substrate RNA," *Nucleic Acids Research* 18:299–304 (1990).

Hampel and Tritz, "RNA Catalytic Properties of the Minimum (–)sTRSV Sequence," *Biochemistry* 28:4929–4933 (1989).

Haseloff and Gerlach, "Simple RNA Enzymes with New and Highly Specific Endoribonuclease Activities," *Nature* 334:585–591 (1988).

Hertel et al., "Numbering System for the Hammerhead," *Nucleic Acids Res.* 20:3252 (1992).

Jeffries and Symons, "A Catalytic 13–mer Ribozyme," *Nucleic Acids Research* 17:1371–1377 (1989).

Kim and Cech, "Three–dimensional model of the active site of the self–splicing rRNA precursor of Tetrahymena," *Proc. Natl. Acad. Sci. USA* 84:8788 (1987).

Mamone et al., "Design of Mannerhead Ribozymes Targeted to Sequences in HIV, HSV, and the RAT ANF GENE," Abstract of Keystone, CO (May 27, 1992).

Ng et al., "Isoguanosine Substitution of Conserved Adenosines in the Hammerhead Ribozyme," *Biochemistry* 33:12119–1216 (1994).

Odai et al., "The role of a conserved guanosine residue in the hammerhead–type RNA enzyme," *FEBS* 267:150–152 (1990).

(List continued on next page.)

Primary Examiner—George C. Elliott
Assistant Examiner—Sean McGarry
Attorney, Agent, or Firm—Lyon & Lyon LLP

[57] ABSTRACT

Method to produce a more active ribozyme by introducing a modified base into a substrate binding arm of the ribozyme or its catalytic core.

9 Claims, 25 Drawing Sheets

OTHER PUBLICATIONS

Pavco et al., "Regulation of Self–Splicing Reactions by Antisense RNA," Abstract of Keystone, CO (May 27, 1992).

Perreault et al., "Mixed Deoxyribo–and Ribo–Oligonucleotides with Catalytic Activity," *Nature* 344:565–567 (1990).

Perrotta and Been, "Cleavage of Oligoribonucleotides by a Ribozyme Derived from the Hepatitis δ Virus RNA Sequence," *Biochemstry* 31:16–21 (1992).

Pieken et al., "Kinetic Characterization of Ribonuclease–Resistant 2'–Modified Hammerhead Ribozymes," *Science* 253:314–317 (1991).

Pyle et al., "Ribozyme Recognition of RNA by Tertiary Interactions with Specific Ribose 2'–H Groups," *Nature* 350:628–631 (1991).

Rossi et al., "Ribozymes as Anti–HIV–1 Therapeutic Agents: Principles, Applications, and Problems," *Aids Research and Human Retroviruses* 8:183–189 (1992).

Saville and Collins, "A Site–Specific Self–Cleavage Reaction Performed by a Novel RNA In Neurospora Mitochondria," *Cell* 61:685–696 (1990).

Saville and Collins, "RNA–Mediated Ligation of Self–Cleavage Products of a Neurospora Mitochondrial Plasmid Transcript." *Proc. Natl. Acad. Sci. USA* 88:8826–8830 (1991).

Scaringe et al., "Chemical synthesis of biologically active oligoribonucleotides using β–cyanoethyl protected ribonucleoside phosphoramidites," *Nucl Acids Res.* 18:5433–5441 (1990).

Seela et al., "122.7–Deazaadenosine: Oligoribonucleotide Building Block Synthesis and Autocatalytic Hydrolysis of Base–Modified Hammerhead Ribozymes," *Helvetica Chimica Acta* 76:1809–1820 (1993).

Slim and Gait, "Configurationally defined phosphorothioate–containing oligoribonucleotides in the study of the mechanism of cleavage of hammerhead ribozymes," *Nucl Acids Res.* 19:1183 (1991).

Tuschl et al., "Importance of Exocyclic Base Functional Groups of Central Core Guanosines for Hammerhead Ribozyme Activity," *Biochemistry* 32:11658–11668 (1993).

Uhlenbeck, "A Small Catalytic Oligoribonucleotide," *Nature* 328:596–600 (1987).

Uhlmann and Peyman, "Antisense Oligonucleotides: A New Therapeutic Principle," *Chemical Reviews* 90:543:584 (1990).

Usman and Cedergren, "Exploiting the chemical synthesis of RNA," *TIBS* 17:334–339 (1992).

Usman et al., "Automated Chemical Synthesis of Long Oligoribonucleotides Using 2'–O–Silylated Ribonucleoside 3'–O–Phosphoramidites on a Controlled–Pore Glass Support: Synthesis of a 43–Nucleotide Sequence Similar to the 3'–Half Molecule of an *Escherichia coli* Formylmethoionine tRNA," *J. Am. Chem. Soc.* 109–7845–7854 (1987).

Vorbruggen et al., "Nucleoside Synthesis with Trimethylsilyl Triflate and Perchlorate as Catalysts," *Chem. Ber.* 114:1234–1255 (1981).

Weerasinghe et al., "Resistance to Human Immunodeficiency Virus Type 1 (HIV–1) Infection in Human CD4$^+$ Lymphocyte–Derived Cell Lines Conferred by Using Retroviral Vectors Expressing an HIV–1 RNA–Specific Ribozyme," *Journal of Virology* 65:5531–5534 (1994).

Dropulic et al., "Functional Characterizarion of a U5 Ribozyme: Intracellular Suppression of Human Immunodeficiency Virus Type 1 Expression," *Journal of Virology* 66:1432–1441 (1992).

He et al., "In Vitro cleavage of HPV16 E6 and E7 mRNA by designed ribozymes," *Chemical Abstracts* vol. 120, No. 1 at abstract No. 3342 (1994).

He et al., "In Vitro cleavage of HPV16 E6 and E7 mRNA by designed ribozymes," *FEBS Letters* 322:21–24 (1993).

Lu et al., "Ribozyme–mediated in vitro cleavage of transcripts arising from the major transforming genes of human papillomavirus type 16," *Cancer Gene Therapy* 1(4):267–277 (1994).

Rossi and Sarver, "RNA enzymes (ribozymes) as antiviral therapeutic agents," *TIBTECH* 8:179–183 (1990).

Rossi et al., "Ribozymes as potential therapeutic agents," *Proc. Annu. Meeting Am. Assoc, Cancer Res.* 34:592–593 (1993).

Rossi et al., "Ribozymes as Therapies For AIDS," *Annals of the New York Academy of Sciences* 606:184–200 (1990).

von Weizsacker et al., "Cleavage of Hepatitis B Virus RNA by Three Ribozymes Transcribed From a Single DNA Template," *Biochemical and Biophysical Research Communications* 189:743–748 (1992).

Wong–Staal, "Molecular targets for interference with viral replication," *International Conference on Aids* 9(1):10 (1993).

Stull et al "Antigen, Ribozyme and Aptomer Nucleic Acid Drugs: Progress & Prospects" *Pharmaceutical Research* vol. 12(4) 1995 pp. 465–483.

Figure 1: The Hammerhead Ribozyme

Figure 2. Hammerhead Ribozyme Substrate Motifs

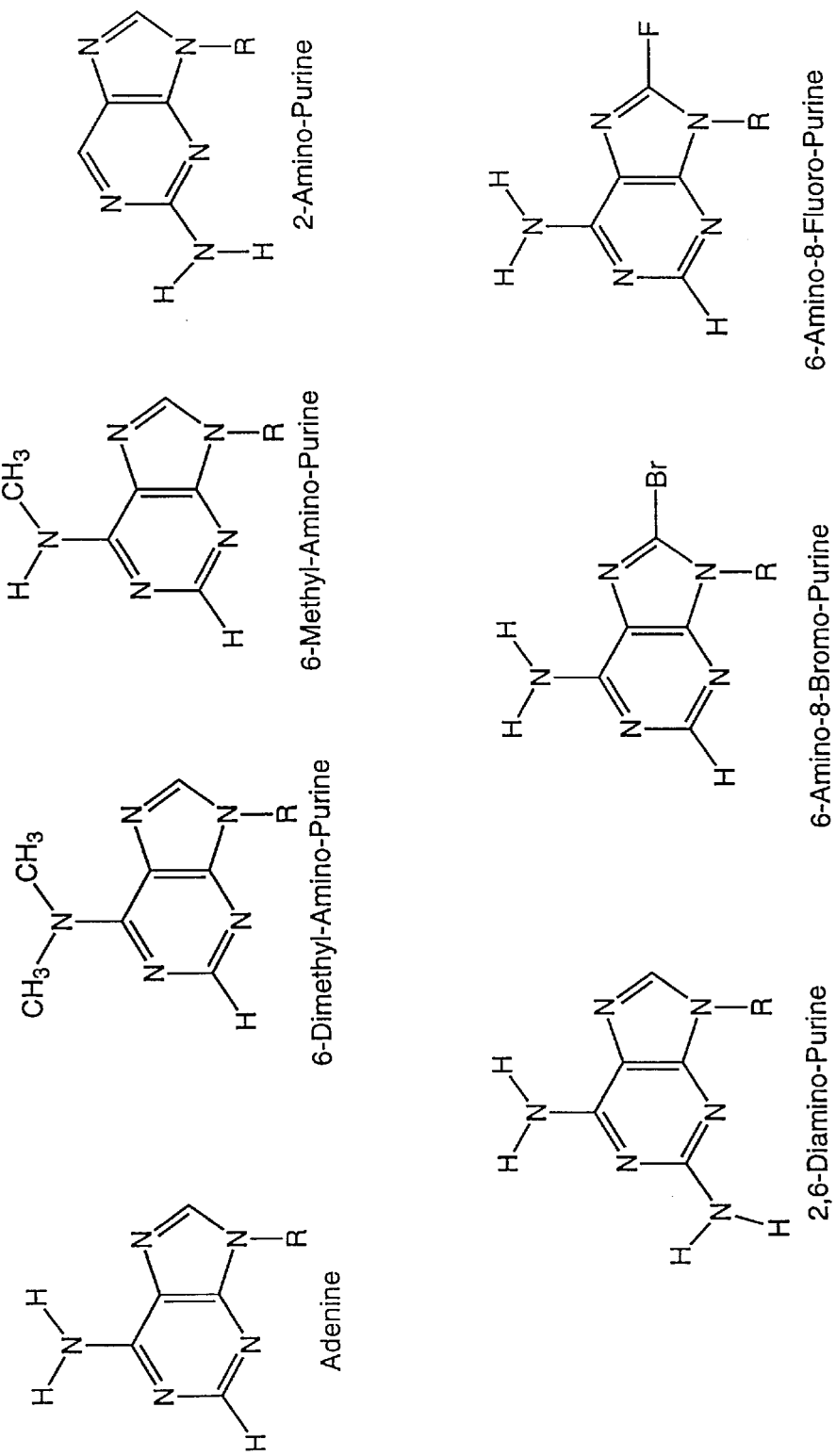
Fig. 6A: Adenine Modifications

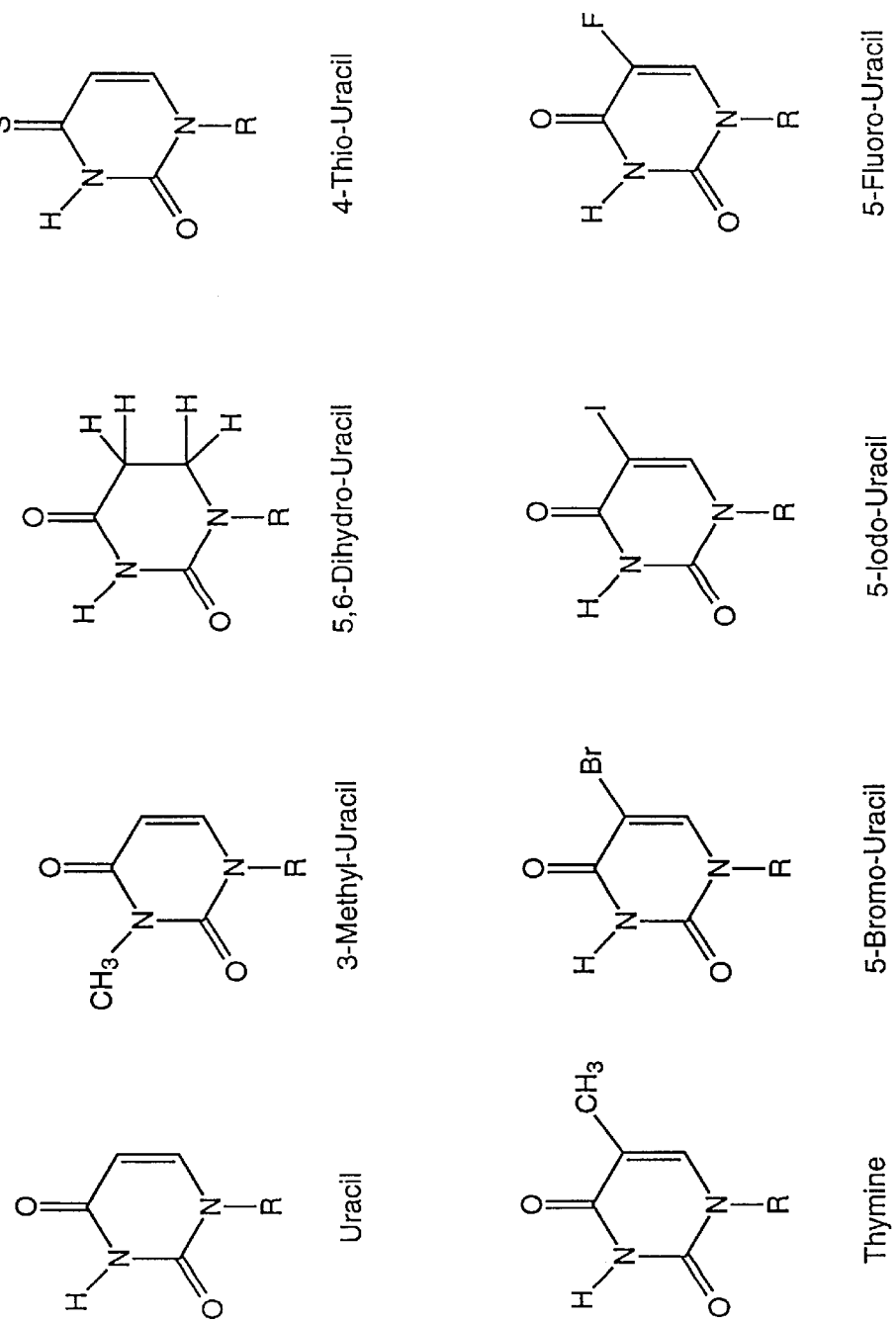
Fig. 6B: Uracil Modifications

*Fig. 6C*: Guanine Modifications
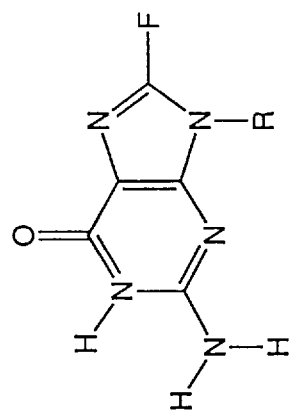
8-Fluoro-Guanine
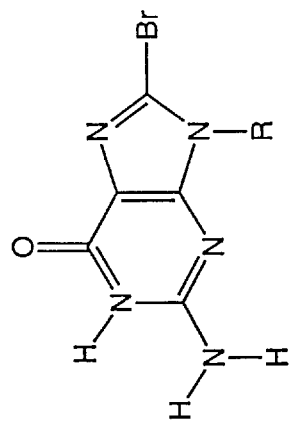
8-Bromo-Guanine
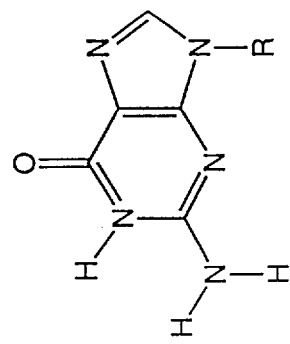
Guanine
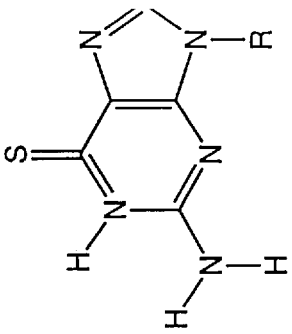
6-Thio-Guanine
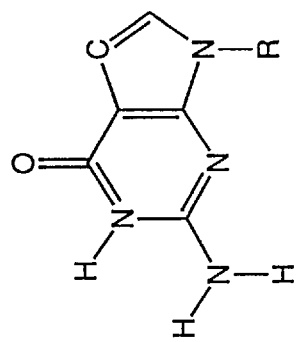
7-Deaza-Guanine
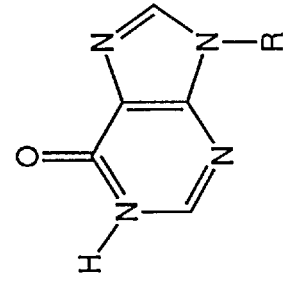
Hypoxanthine (Inosine base)
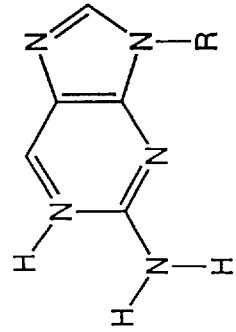
2-Amino-Purine

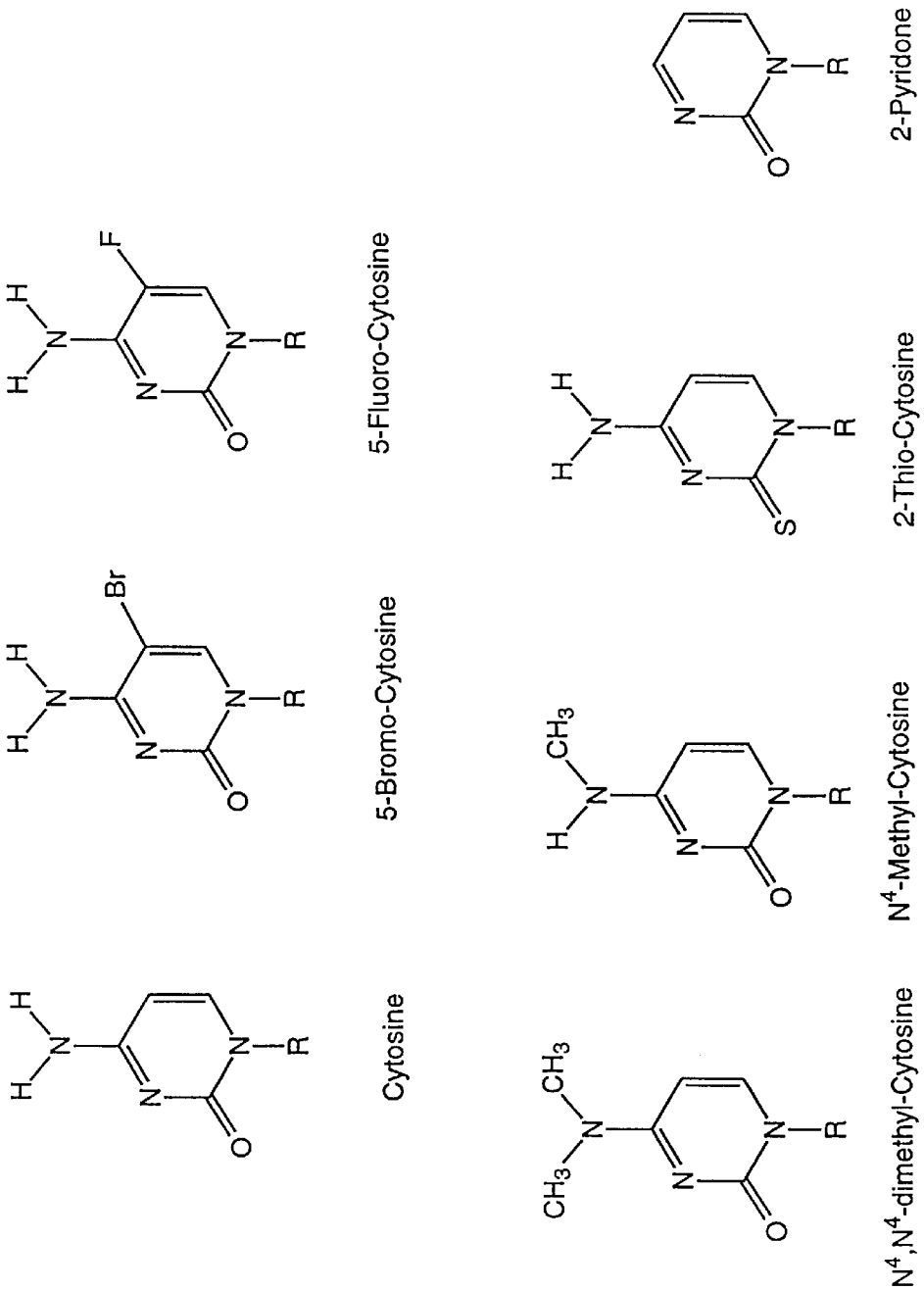
Fig. 6D: Cytosine Modifications

Modified-Base Containing Catalytic Nucleic Acid

Fig. 8: Base-Modified Nucleotides
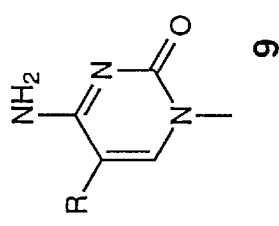
4  5-Alkyluridine
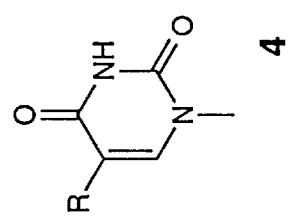
9  5-Alkylcytidine
13  5-Halouridine
17  6-Azauridine
22  Diaminopurine
23  Purine
B =
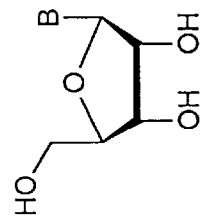

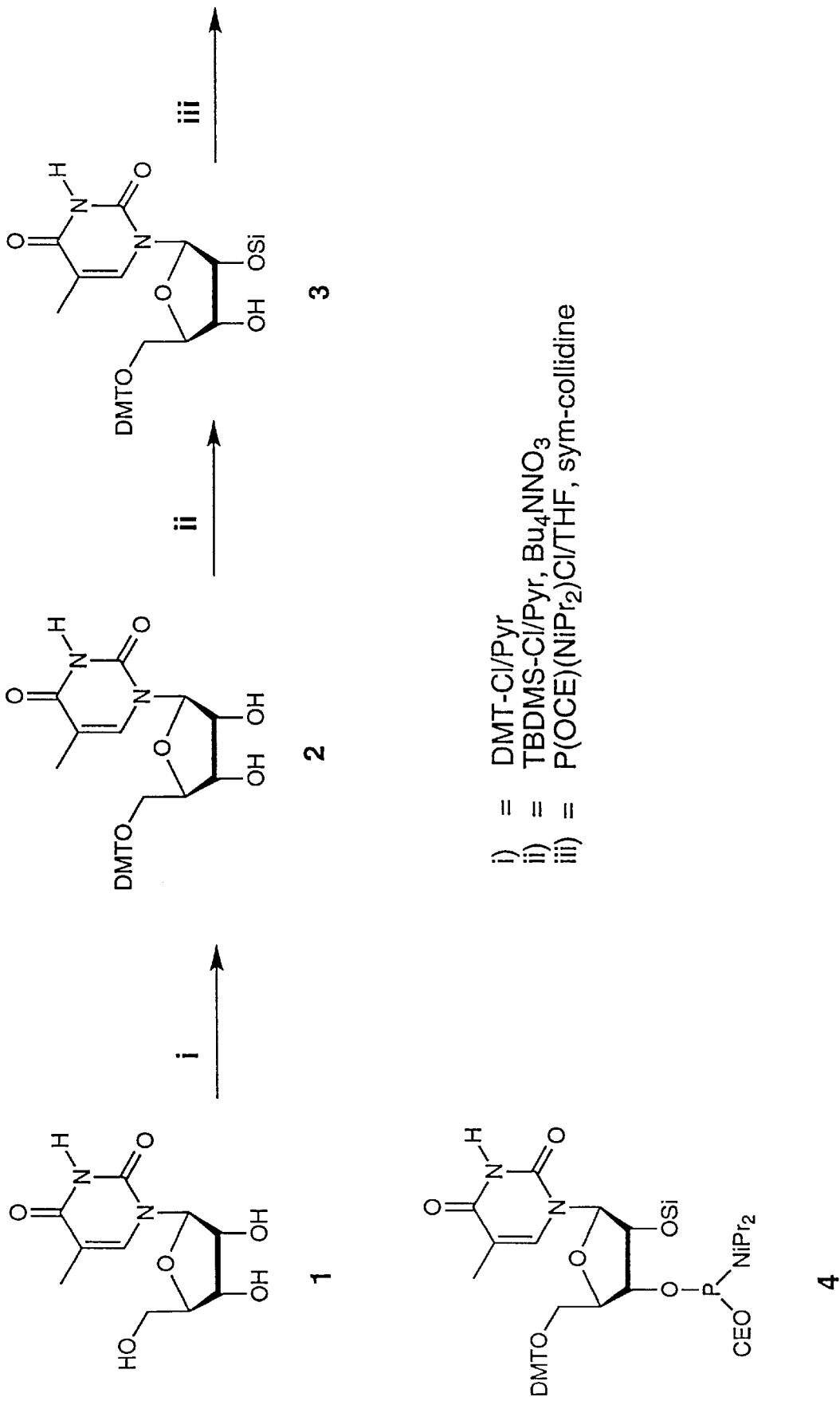
Fig. 9: Synthesis of Ribothymidine Phosphoramidite

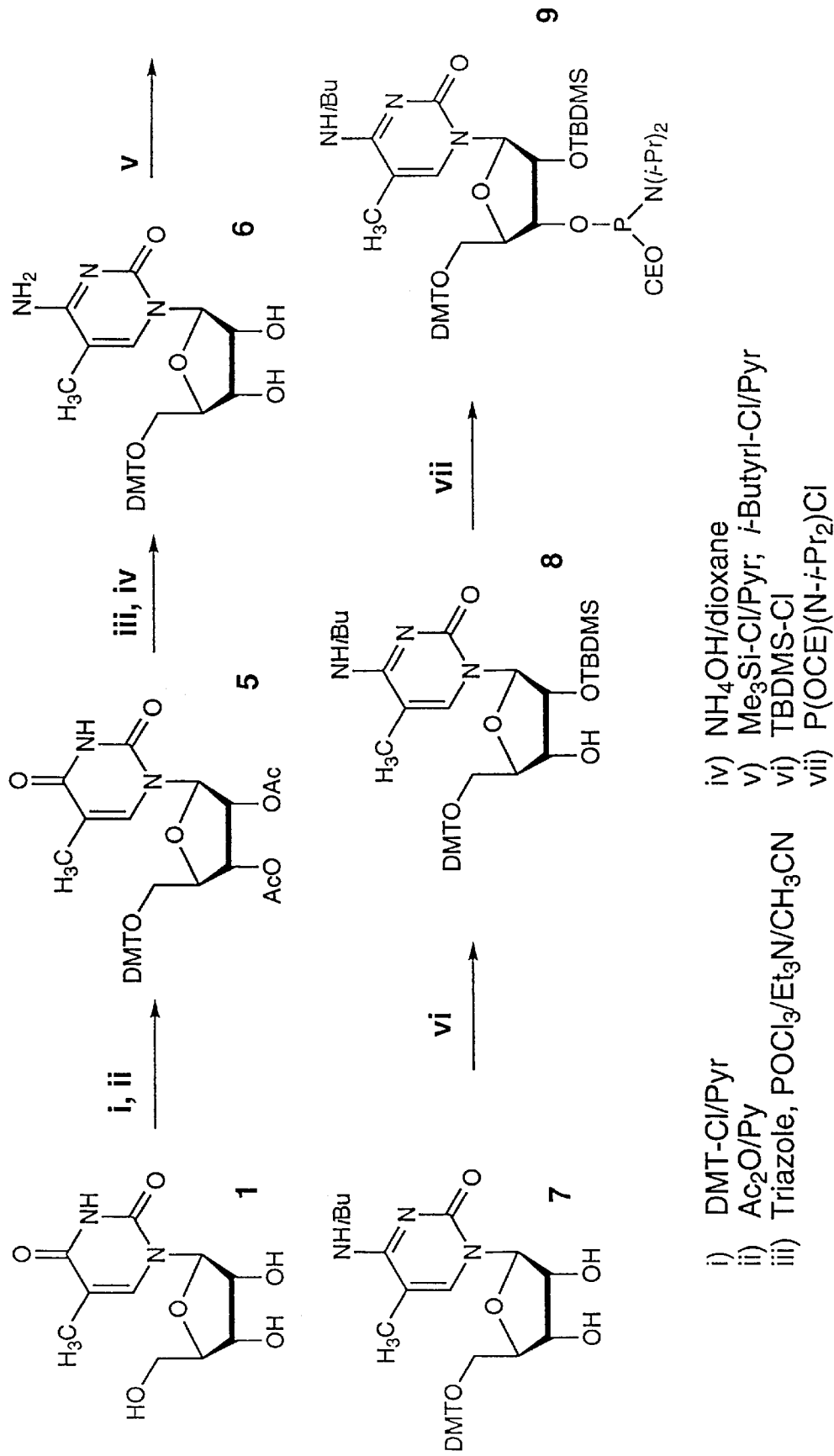
Fig. 10: Synthesis of 5-Methylcytidine Phosphoramidite

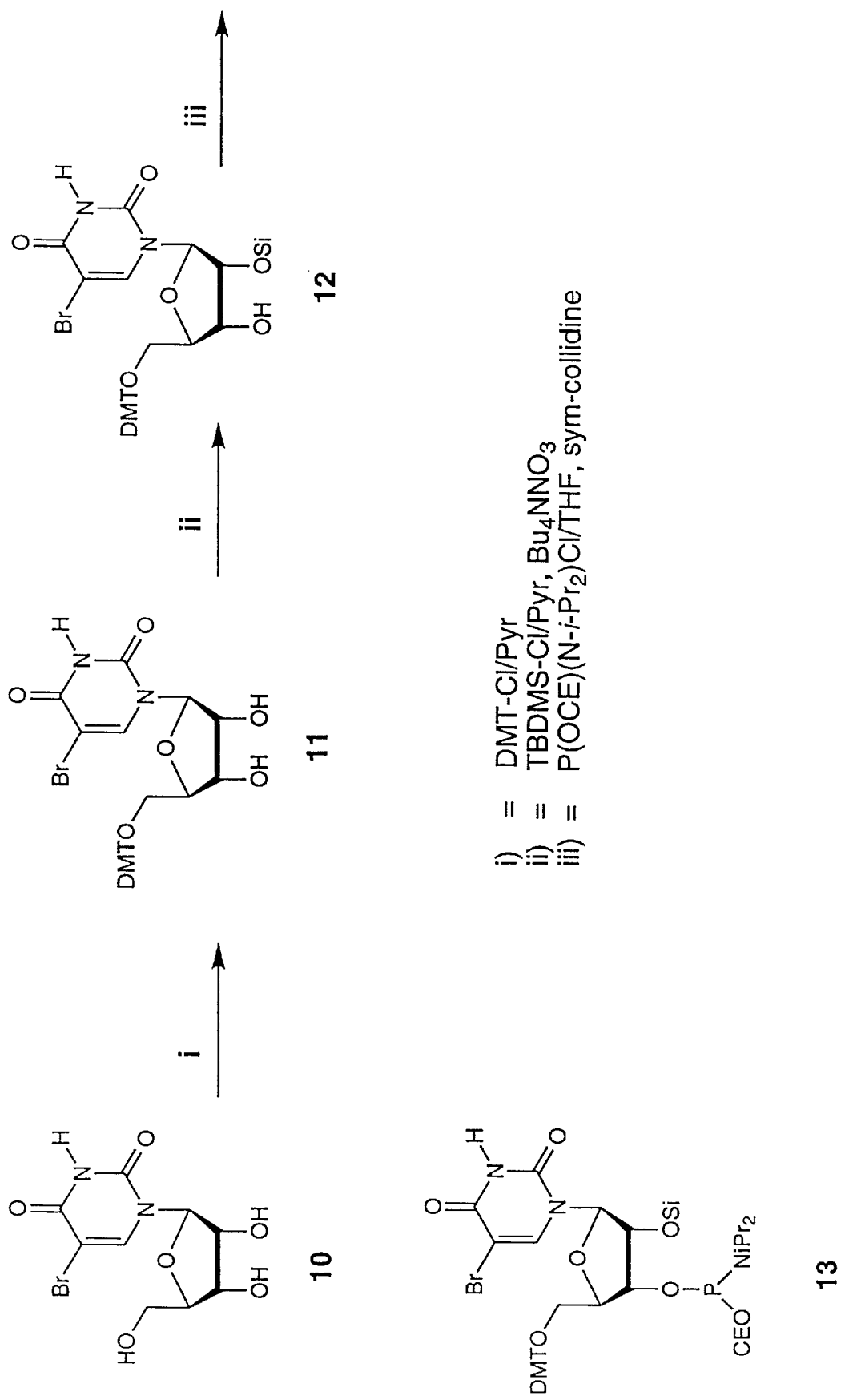
Fig. 11: Synthesis of 5-Bromouridine Phosphoramidite

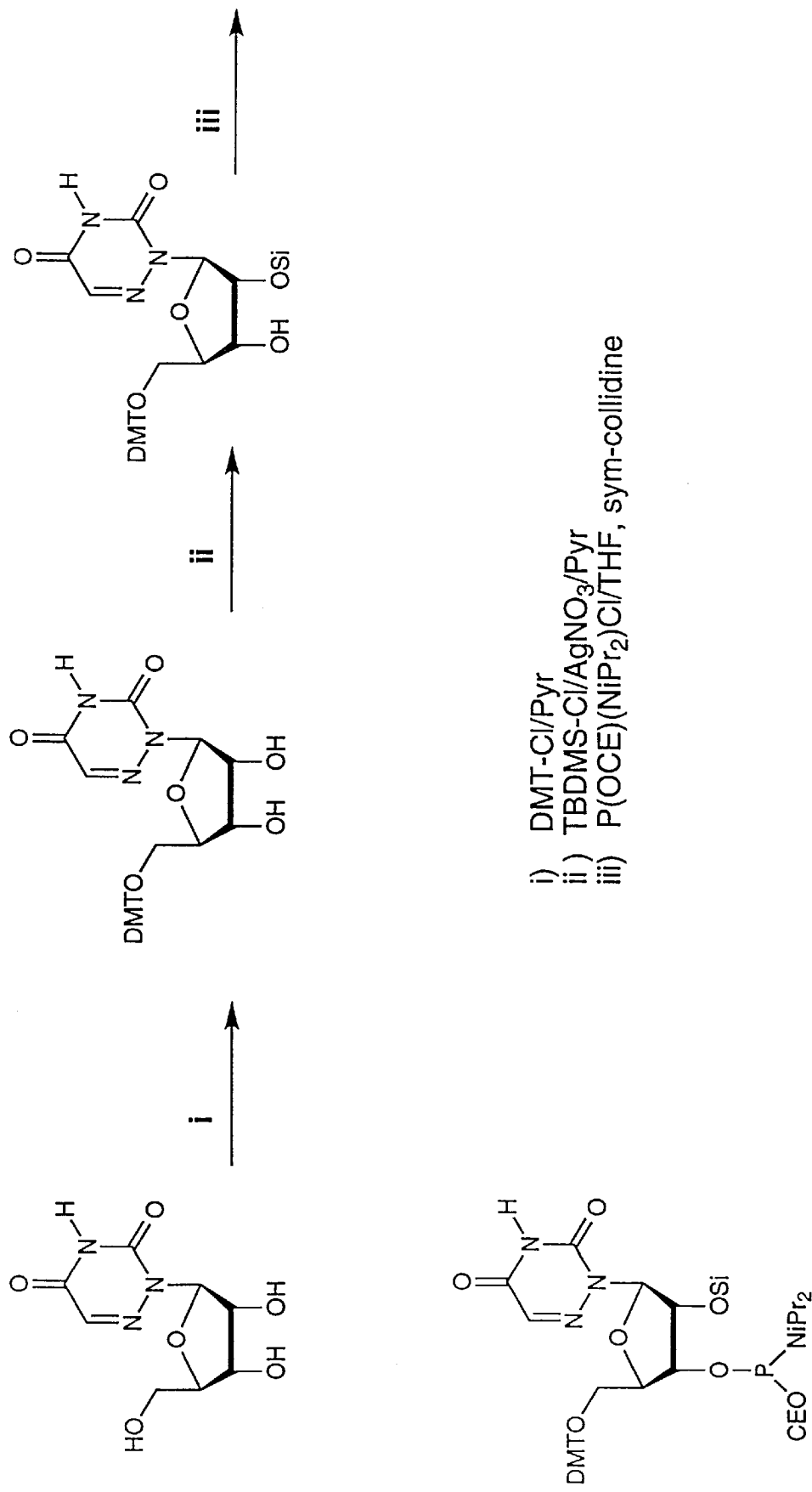
Fig. 12 Synthesis of 6-Azauridine Phosphoramidite
i) DMT-Cl/Pyr
ii) TBDMS-Cl/AgNO$_3$/Pyr
iii) P(OCE)(NiPr$_2$)Cl/THF, sym-collidine

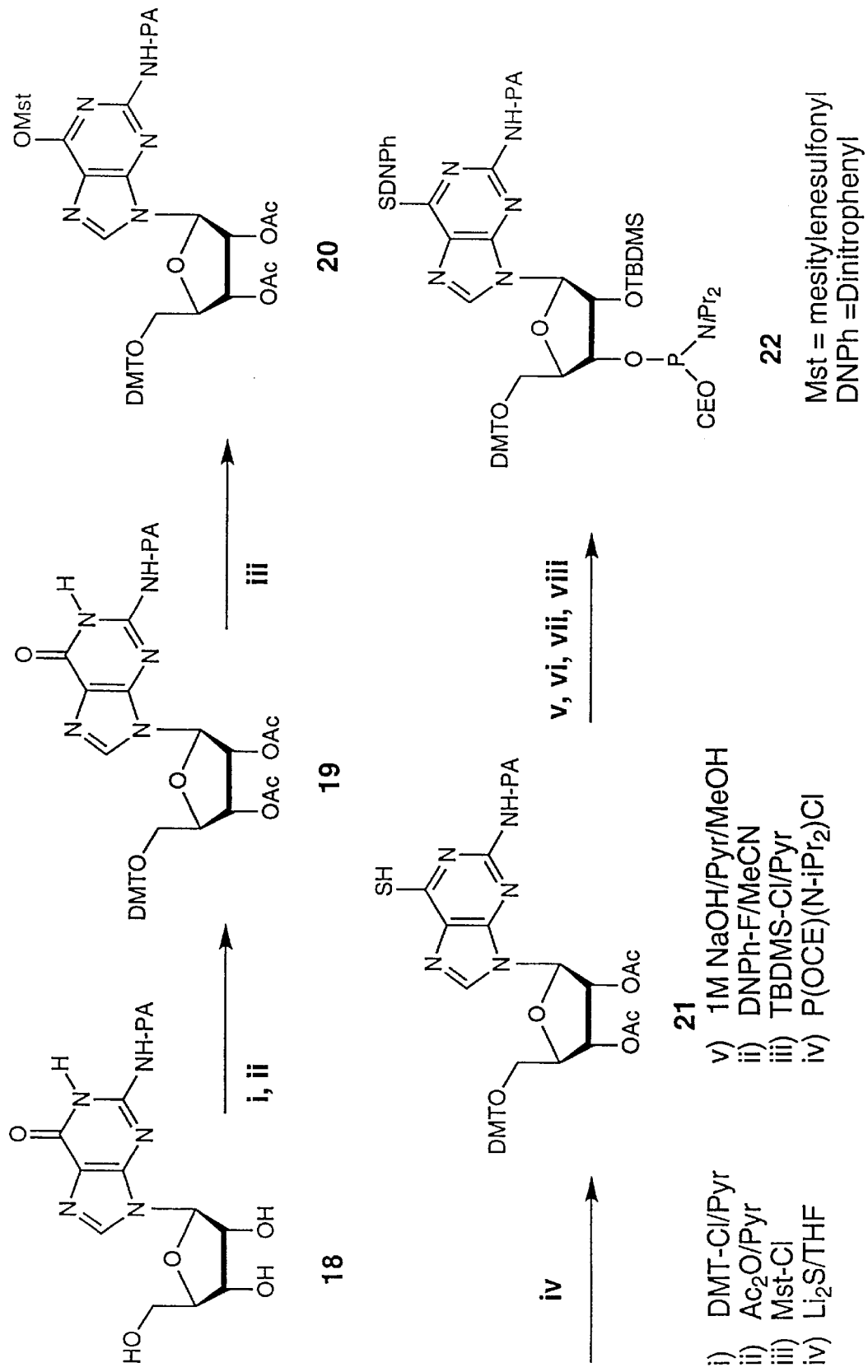
Fig. 13: Synthesis of Diaminopurine Phosphoramidite

Fig. 14: Synthesis of 6-Methyl- Uridine Phosphoramidites
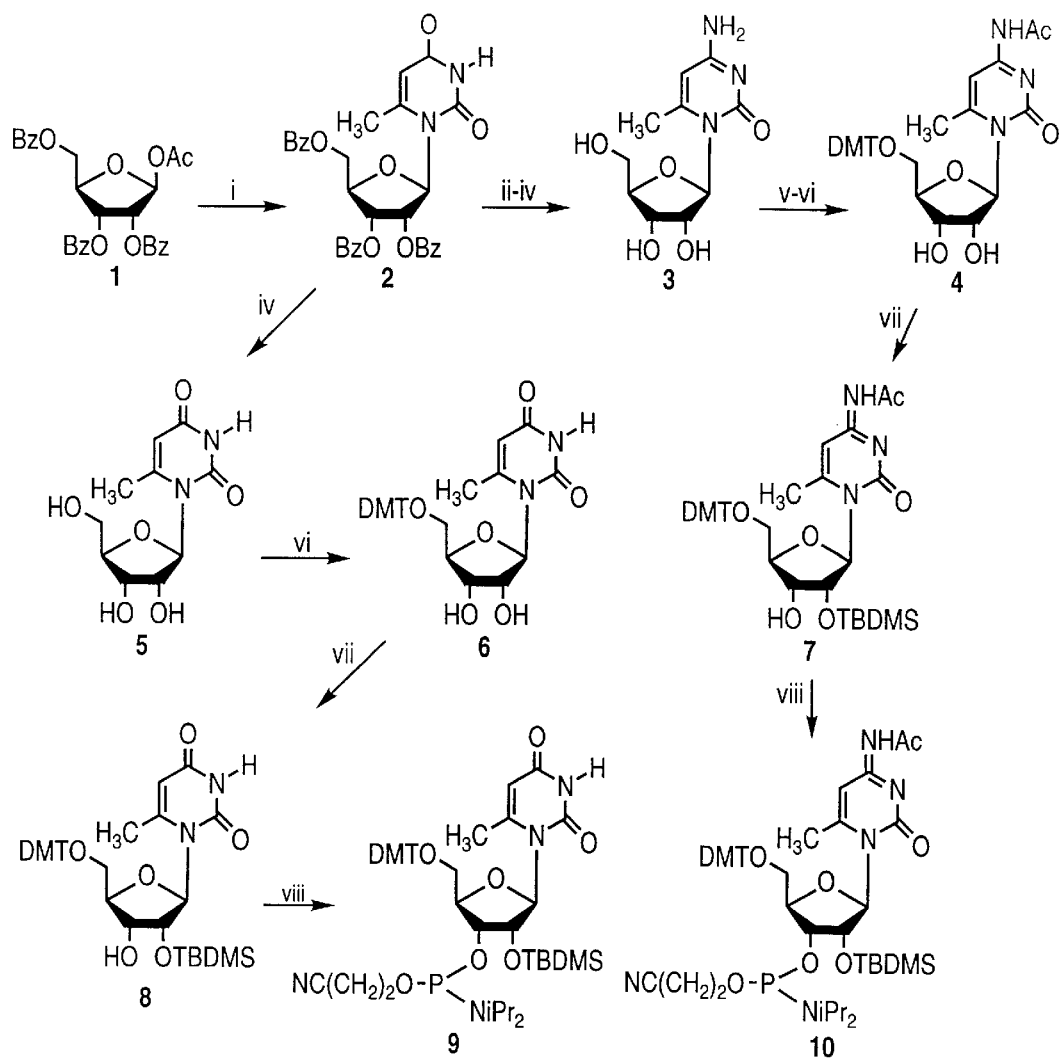
Reagents and Conditions: i) 6-Me-Ura^TMS, CF$_3$SO$_3$SiMe$_3$, 0 °C; ii) 1,2,4-triazole, POCl$_3$; iii) NH$_4$OH/dioxane; iv) 2M NaOH/Pyr/MeOH; v) Me$_3$Si-Cl/Pyr, then Ac$_2$O; vi) DMT-Cl/Pyr; vii) TBDMS-Cl/AgNO$_3$/Pyr/THF; viii) 2-cyanoethyl-N,N-diisopropylchlorophosphoramidite, DIPEA/CH$_2$Cl$_2$.

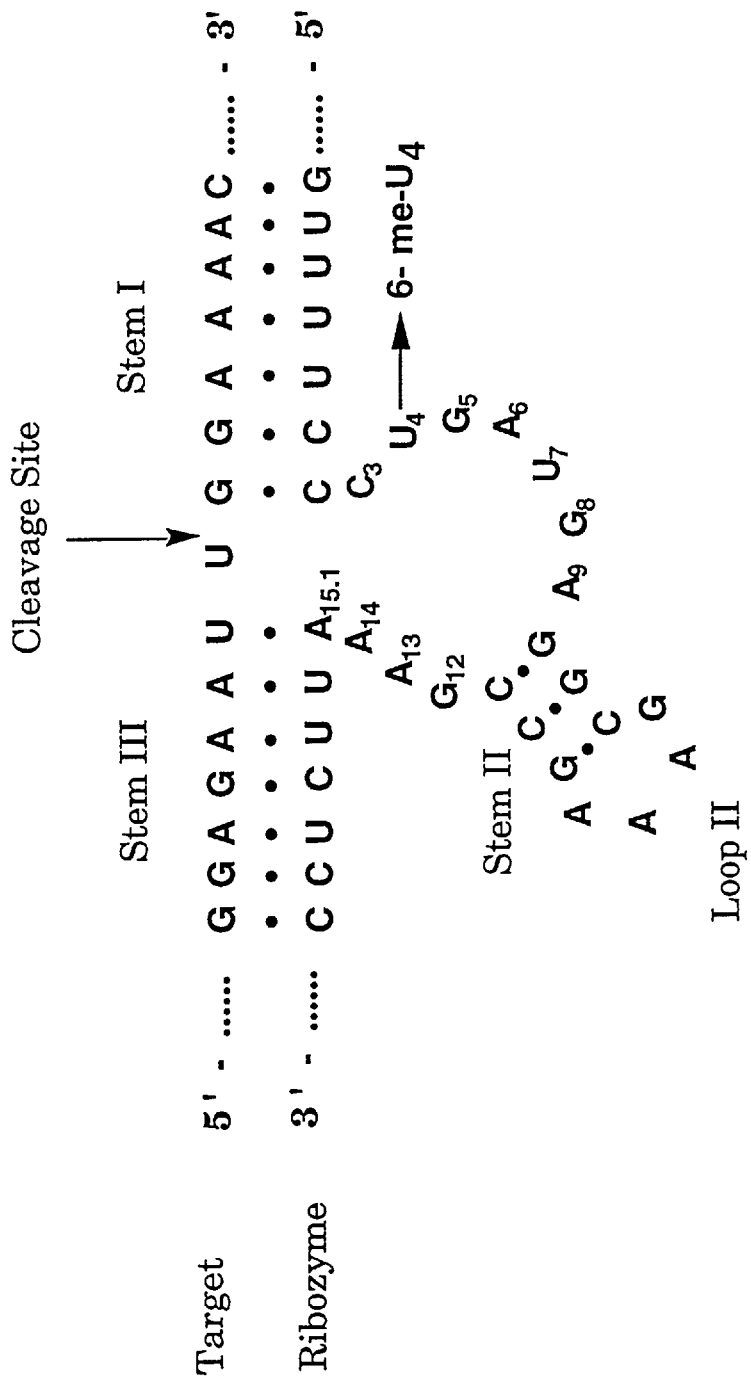
Fig. 15: Hammerhead Ribozyme to Site A (HHA)

RNA Cleavage Catalyzed by 6-Methyl-U-Substituted HHA Ribozyme

[Ribozyme] = 40 nM  [Substrate] = ~1 nM

*Fig. 17*: Hammerhead Ribozyme to Site B (HHB)

*Fig. 19:* Hammerhead Ribozyme to Site C (HHC)

RNA Cleavage Catalyzed by 6-Methyl-U-Substituted HHC Ribozyme

[Ribozyme] = 40 nM  [Substrate] = ~1 nM

SEQUENCE LISTING ( 1 ) GENERAL INFORMATION:

( i i i ) NUMBER OF SEQUENCES: 14

( 2 ) INFORMATION FOR SEQ ID NO: 1:

( i ) SEQUENCE CHARACTERISTICS:
        ( A ) LENGTH: 11
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"
            stands for any base.
            " H"represents
            nucleotide C, A, or
            U.

( i i ) SEQUENCE DESCRIPTION: SEQ ID NO: 1:

N N N N U H N N N N   N         1 1

( 2 ) INFORMATION FOR SEQ ID NO: 2:

( i ) SEQUENCE CHARACTERISTICS:
        ( A ) LENGTH: 28
        ( B ) TYPE: nucleic acid
        ( C ) STRANDEDNESS: single
        ( D ) TOPOLOGY: linear (ix) FEATURE:
                (D) OTHER INFORMATION: The letter "N"
                        stands for any base.

(ii) SEQUENCE DESCRIPTION: SEQ ID NO: 2:

NNNNNCUGAN GAGNNNNNNC GAAANNNN                                                          28

(2) INFORMATION FOR SEQ ID NO: 3:

(i) SEQUENCE CHARACTERISTICS:
                (A) LENGTH: 16
                (B) TYPE: nucleic acid
                (C) STRANDEDNESS: single
                (D) TOPOLOGY: linear (ix) FEATURE:
                (D) OTHER INFORMATION: The letter "N"
                        stands for any base.
                        The leter "Y"is U
                        or C. The letter
                        "H"is A, U, or C.

(ii) SEQUENCE DESCRIPTION: SEQ ID NO: 3:

NNNYHGNYNN NNNNNN                                                                        16

(2) INFORMATION FOR SEQ ID NO: 4:

(i) SEQUENCE CHARACTERISTICS:
                (A) LENGTH: 47
                (B) TYPE: nucleic acid
                (C) STRANDEDNESS: single
                (D) TOPOLOGY: linear (ix) FEATURE:
                (D) OTHER INFORMATION: The letter "N"
                        stands for any base.

(ii) SEQUENCE DESCRIPTION: SEQ ID NO: 4:

NNNNNNNNC AUUACANNNN NNNAHAAANN NNNNNNNNG AAGNNNN                                        47

(2) INFORMATION FOR SEQ ID NO: 5:

(i) SEQUENCE CHARACTERISTICS:
                (A) LENGTH: 85
                (B) TYPE: nucleic acid
                (C) STRANDEDNESS: single
                (D) TOPOLOGY: linear (ii) SEQUENCE DESCRIPTION: SEQ ID NO: 5:

UGGCCGGCAU GGUCCAGCC UCCUCGCUGG CGCCGGCUGG GCAACAUUCC                                    50

GAGGGGACCG UCCCCUCGGU AAUGGCGAAU GGGAC                                                   85

(2) INFORMATION FOR SEQ ID NO: 6:

(i) SEQUENCE CHARACTERISTICS:
                (A) LENGTH: 176
                (B) TYPE: nucleic acid
                (C) STRANDEDNESS: single
                (D) TOPOLOGY: linear (ii) SEQUENCE DESCRIPTION: SEQ ID NO: 6:

GGGAAAGCUU GCGAAGGGCG UCGUCGCCCC GAGCGGUAGU AAGCAGGGAA                                   50

CUCACCUCCA AUUUCAGUAC UGAAAUUGUC GUAGCAGUUG ACUACUGUUA                                   100

UGUGAUUGGU AGAGGCUAAG UGACGGUAUU GGCGUAAGUC AGUAUUGCAG                                   150

CACAGCACAA GCCCGCUUGC GAGAAU                                                             176

( 2 ) INFORMATION FOR SEQ ID NO: 7:

( i ) SEQUENCE CHARACTERISTICS:
        ( A ) LENGTH: 15
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"
            stands for any base.

( i i ) SEQUENCE DESCRIPTION: SEQ ID NO: 7:

NNNNNNUHNN NNNNN                                        15

( 2 ) INFORMATION FOR SEQ ID NO: 8:

( i ) SEQUENCE CHARACTERISTICS:
        ( A ) LENGTH: 28
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"
            stands for any base.

( i i ) SEQUENCE DESCRIPTION: SEQ ID NO: 8:

NNNNNNNCUG ANGAGNNCGA AANNNNNN                    28

( 2 ) INFORMATION FOR SEQ ID NO: 9:

( i ) SEQUENCE CHARACTERISTICS:
        ( A ) LENGTH: 15
        ( B ) TYPE: nucleic acid
        ( C ) STRANDEDNESS: single
        ( D ) TOPOLOGY: linear ( i i ) SEQUENCE DESCRIPTION: SEQ ID NO: 9:

CAAAAGGUUA AGAGG                                        15

( 2 ) INFORMATION FOR SEQ ID NO: 10:

( i ) SEQUENCE CHARACTERISTICS:
        ( A ) LENGTH: 35
        ( B ) TYPE: nucleic acid
        ( C ) STRANDEDNESS: single
        ( D ) TOPOLOGY: linear ( i i ) SEQUENCE DESCRIPTION: SEQ ID NO: 10:

CCUCUUAAAG CCGAAAGCGG AGUAGUUCCC UUUUG              35

( 2 ) INFORMATION FOR SEQ ID NO: 11:

( i ) SEQUENCE CHARACTERISTICS:
        ( A ) LENGTH: 15
        ( B ) TYPE: nucleic acid
        ( C ) STRANDEDNESS: single
        ( D ) TOPOLOGY: linear ( i i ) SEQUENCE DESCRIPTION: SEQ ID NO: 11:

AGAGGUAAUU AGGGA                                        15

( 2 ) INFORMATION FOR SEQ ID NO: 12:

( i ) SEQUENCE CHARACTERISTICS:
        ( A ) LENGTH: 35
        ( B ) TYPE: nucleic acid
        ( C ) STRANDEDNESS: single -continued (D) TOPOLOGY: linear (i i) SEQUENCE DESCRIPTION: SEQ ID NO: 12:

UCCCUAAAAG CCGAAAGCGG AGUUAGUCUA CCUCU   35

(2) INFORMATION FOR SEQ ID NO: 13:

(i) SEQUENCE CHARACTERISTICS:
    (A) LENGTH: 15
    (B) TYPE: nucleic acid
    (C) STRANDEDNESS: single
    (D) TOPOLOGY: linear (i i) SEQUENCE DESCRIPTION: SEQ ID NO: 13:

UAAGAAGUUU UUGUC   15

(2) INFORMATION FOR SEQ ID NO: 14:

(i) SEQUENCE CHARACTERISTICS:
    (A) LENGTH: 36
    (B) TYPE: nucleic acid
    (C) STRANDEDNESS: single
    (D) TOPOLOGY: linear (i i) SEQUENCE DESCRIPTION: SEQ ID NO: 14:

GACAUAAAAG CCGAAAGCGG AGUUAGUUCC UUCUUA   36

BASE-MODIFIED ENZYMATIC NUCLEIC ACID

This application is a division of Usman et., U.S. Ser. No. 08/363,254, filed Dec. 23, 1994, (hereby incorporated by reference herein in totality, including drawings) which is a continuation-in-part of McSwiggen, "Optimization of Ribozyme Activity", U.S. Ser. No. 07/963,322, filed Oct. 15, 1992, now abandoned, and Usman et al., entitled "Base-modified enzymatic nucleic acid", U.S. Ser. No. 08/149,210 (filed Nov. 8, 1993), now abandoned, the whole of both of which, including drawings, is hereby incorporated by reference herein.

BACKGROUND OF THE INVENTION

This invention relates to enzymatic RNA molecules or ribozymes having a modified nucleotide base sequence.

Ribozymes are RNA molecules having an enzymatic activity which is able to repeatedly cleave other separate RNA molecules in a nucleotide base sequence specific manner. Such enzymatic RNA molecules can be targeted to virtually any RNA transcript, and efficient cleavage achieved in vitro. Kim et al., 84 *Proc. Natl. Acad. Sci. USA* 8788, 1987; Haseloff and Gerlach, 334 *Nature* 585, 1988; Cech, 260 *JAMA* 3030, 1988; and Jefferies et al., 17 *Nucleic Acids Research* 1371, 1989.

Ribozymes act by first binding to a target RNA. Such binding occurs through the target RNA binding portion of a ribozyme which is held in close proximity to an enzymatic portion of the RNA which acts to cleave the target RNA. Thus, the ribozyme first recognizes and then binds a target RNA through complementary base-pairing, and once bound to the correct site, acts enzymatically to cut the target RNA. Strategic cleavage of such a target RNA will destroy its ability to direct synthesis of an encoded protein. After a ribozyme has bound and cleaved its RNA target it is released from that RNA to search for another target and can repeatedly bind and cleave new targets.

By "complementarity" is meant a nucleic acid that can form hydrogen bond(s) with other RNA sequence by either traditional Watson-Crick or other non-traditional types (for example, Hoogsteen type) of base-paired interactions.

Six basic varieties of naturally-occurring enzymatic RNAs are known presently. Each can catalyze the hydrolysis of RNA phosphodiester bonds in trans (and thus can cleave other RNA molecules) under physiological conditions. Table I summarizes some of the characteristics of these ribozymes. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over other technologies, such as antisense technology (where a nucleic acid molecule simply binds to a nucleic acid target to block its translation) since the effective concentration of ribozyme necessary to effect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding, but also on the mechanism by which the molecule inhibits the expression of the RNA to which it binds. That is, the inhibition is caused by cleavage of the RNA target and so specificity is defined as the ratio of the rate of cleavage of the targeted RNA over the rate of cleavage of non-targeted RNA. This cleavage mechanism is dependent upon factors additional to those involved in base pairing. Thus, it is thought that the specificity of action of a ribozyme is greater than that of antisense oligonucleotide binding the same RNA site.

The following discussion of relevant art is dependent on the diagram shown in FIG. 1, in which the numbering of various nucleotides in a hammerhead ribozyme is provided. This is not to be taken as an indication that the Figure is prior art to the pending claims, or that the art discussed is prior art to those claims.

Odai et al., *FEBS* 1990, 267:150, state that substitution of guanosine (G) at position 5 of a hammerhead ribozyme for inosine greatly reduces catalytic activity, suggesting "the importance of the 2-amino group of this guanosine for catalytic activity."

Fu and McLaughlin, *Proc. Natl. Acad. Sci. (USA)* 1992, 89:3985, state that deletion of the 2-amino group of the guanosine at position 5 of a hammerhead ribozyme, or deletion of either of the 2'-hydroxyl groups at position 5 or 8, resulted in ribozymes having a decrease in cleavage efficiency.

Fu and McLaughlin, *Biochemistry* 1992, 31:10941, state that substitution of 7-deazaadenosine for adenosine residues in a hammerhead ribozyme can cause reduction in cleavage efficiency. They state that the "results suggest that the $N^7$-nitrogen of the adenosine (A) at position 6 in the hammerhead ribozyme/substrate complex is critical for efficient cleavage activity." They go on to indicate that there are five critical functional groups located within the tetrameric sequence GAUG in the hammerhead ribozyme.

Slim and Gait, 1992, *BBRC* 183, 605, state that the substitution of guanosine at position 12, in the core of a hammerhead ribozyme, with inosine inactivates the ribozyme.

Tuschl et al., 1993 *Biochemistry* 32, 11658, state that substitution of guanosine residues at positions 5, 8 and 12, in the catalytic core of a hammerhead, with inosine, 2-aminopurine, xanthosine, isoguanosine or deoxyguanosine cause significant reduction in the catalytic efficiency of a hammerhead ribozyme.

Fu et al., 1993 *Biochemistry* 32, 10629, state that deletion of guanine $N^7$, guanine $N^2$ or the adenine $N^6$-nitrogen within the core of a hammerhead ribozyme causes significant reduction in the catalytic efficiency of a hammerhead ribozyme.

Grasby et al., 1993 *Nucleic Acids Res.* 21, 4444, state that substitution of guanosine at position s 5, 8 and 12 position s within the core of a hammerhead ribozyme with $O^6$-methylguanosine results in an approximately 75-fold reduction in $k_{cat}$.

Seela et al., 1993 *Helvetica Chimica Acta* 76, 1809, state that substitution of adenine at positions 13, 14 and 15, within the core of a hammerhead ribozyme, with 7-deazaadenosine does not significantly decrease the catalytic efficiency of a hammerhead ribozyme.

Adams et al., 1994 *Tetrahedron Letters* 35, 765, state that substitution of uracil at position 17 within the hammerhead ribozyme.substrate complex with 4-thiouridine results in a reduction in the catalytic efficiency of the ribozyme by 50 percent.

Ng et al., 1994 *Biochemistry* 33, 12119, state that substitution of adenine at positions 6, 9 and 13 within the catalytic core of a hammerhead ribozyme with isoguanosine, significantly decreases the catalytic activity of the ribozyme.

Jennings et al., U.S. Pat. No. 5,298,612, indicate that nucleotides within a "minizyme" can be modified. They state "Nucleotides comprise a base, sugar and a monophosphate group. Accordingly, nucleotide derivatives or modifications may be made at the level of the base, sugar or monophosphate groupings . . . Bases may be substituted with various groups, such as halogen, hydroxy, amine, alkyl, azido, nitro, phenyl and the like."

SUMMARY OF THE INVENTION

This invention relates to production of enzymatic RNA molecules or ribozymes having enhanced or reduced binding affinity and enhanced enzymatic activity for their target nucleic acid substrate by inclusion of one or more modified nucleotides in the substrate binding portion of a ribozyme such as a hammerhead, hairpin, VS ribozyme or hepatitis delta virus derived ribozyme. Applicant has recognized that only small changes in the extent of base-pairing or hydrogen bonding between the ribozyme and substrate can have significant effect on the enzymatic activity of the ribozyme on that substrate. Thus, applicant has recognized that a subtle alteration in the extent of hydrogen bonding along a substrate binding arm of a ribozyme can be used to improve the ribozyme activity compared to an unaltered ribozyme containing no such altered nucleotide. Thus, for example, a guanosine base may be replaced with an inosine to produce a weaker interaction between a ribozyme and its substrate, or a uracil may be replaced with a bromouracil (BrU) to increase the hydrogen bonding interaction with an adenosine. Other examples of alterations of the four standard ribonucleotide base s are shown in FIGS. 6a–d with weaker or stronger hydrogen bonding abilities shown in each figure.

In addition, applicant has determined that base modification within some catalytic core nucleotides maintains or enhances enzymatic activity compared to an unmodified molecule. Such nucleotide s are noted in FIG. 7. Specifically, referring to FIG. 7, the preferred sequence of a hammerhead ribozyme in a 5' to 3' direction of the catalytic core is CUG ANG A G.C GAAA, wherein N can be any base or may lack a base (abasic); G.C is a base-pair. The nature of the base-paired stem II (FIGS. 1, 2 and 7) and the recognition arms of stems I and III are variable. In this invention, the use of base-modified nucleotides in those regions that maintain or enhance the catalytic activity and/or the nuclease resistance of the hammerhead ribozyme are described. (Bases which can be modified include those shown in capital letters).

Examples of base-substitutions useful in this invention are shown in FIG. 6, 8–14. In preferred embodiments cytidine residues are substituted with 5-alkylcytidines (e.g., 5-methylcytidine, FIG. 8, R=CH$_3$, 9), and uridine residues with 5-alkyluridines (e.g., ribothymidine (FIG. 8, R=CH$_3$, 4) or 5-halouridine (e.g., 5-bromouridine, FIG. 8, X=Br, 1 3) or 6-azapyrimidines (FIG. 8, 17) or 6-alkyluridine (FIG. 14). Guanosine or adenosine residues may be replaced by diaminopurine residues (FIG. 8, 22) in either the core or stems. In those bases where none of the functional groups are important in the complexing of magnesium or other functions of a ribozyme, they are optionally replaced with a purine ribonucleoside (FIG. 8, 23), which significantly reduces the complexity of chemical synthesis of ribozymes, as no base-protecting group is required during chemical incorporation of the purine nucleus. Furthermore, as discussed above, base-modified nucleotides may be used to enhance the specificity or strength of binding of the recognition arms with similar modifications. Base-modified nucleotides, in general, may also be used to enhance the nuclease resistance of the catalytic nucleic acids in which they are incorporated. These modifications within the hammerhead ribozyme motif are meant to be non-limiting example. Those skilled in the art will recognize that other ribozyme motifs with similar modifications can be readily synthesized and are within the scope of this invention.

Substitutions of sugar moieties as described in the art cited above, may also be made to enhance catalytic activity and/or nuclease stability.

Thus, in a first aspect, the invention features a modified ribozyme having one or more substrate binding arms including one or more modified nucleotide bases; and in a related aspect, the invention features a method for production of a more active modified ribozyme (compared to an unmodified ribozyme) by inclusion of one or more of such modified nucleotide bases in a substrate binding arm.

The invention provides ribozymes having increased enzymatic activity in vitro and in vivo as can be measured by standard kinetic assays. Thus, the kinetic features of the ribozyme are enhanced by selection of appropriate modified bases in the substrate binding arms. Applicant recognizes that while strong binding to a substrate by a ribozyme enhances specificity, it may also prevent separation of the ribozyme from the cleaved substrate. Thus, applicant provides means by which optimization of the base pairing can be achieved. Specifically, the invention features ribozymes with modified bases with enzymatic activity at least 1.5 fold (preferably 2 or 3 fold) or greater than the unmodified corresponding ribozyme. The invention also features a method for optimizing the kinetic activity of a ribozyme by introduction of modified bases into a ribozyme and screening for those with higher enzymatic activity. Such selection may be in vitro or in vivo. By enchanced activity is meant to include activity measured in vivo where the activity is a reflection of both catalytic activity and ribozyme stability. In this invention, the product of these properties in increased or not significantly (less that 10 fold) decreased in vivo compared to an all RNA ribozyme.

By "enzymatic portion" is meant that part of the ribozyme essential for cleavage of an RNA substrate.

By "substrate binding arm" is meant that portion of a ribozyme which is complementary to (i.e., able to base-pair with) a portion of its substrate. Generally, such complementarity is 100%, but can be less if desired. For example, as few as 10 bases out of 14 may be base-paired. Such arms are shown generally in FIGS. 1–3 as discussed below. That is, these arms contain sequences within a ribozyme which are intended to bring ribozyme and target RNA together through complementary base-pairing interactions; e.g., ribozyme sequences within stems I and III of a standard hammerhead ribozyme make up the substrate-binding domain (see FIG. 1).

By "unmodified nucleotide base" is meant one of the bases adenine, cytosine, guanosine, uracil joined to the 1' carbon of β-D-ribo-furanose. The sugar also has a phosphate bound to the 5' carbon. These nucleotides are bound by a phosphodiester between the 3' carbon of one nucleotide and the 5' carbon of the next nucleotide to form RNA.

By "modified nucleotide base" is meant any nucleotide base which contains a modification in the chemical structure of an unmodified nucleotide base which has an effect on the ability of that base to hydrogen bond with its normal complementary base, either by increasing the strength of the hydrogen bonding or by decreasing it (e.g., as exemplified above for inosine and bromouracil). Other examples of modified bases include those shown in FIGS. 6a–d and other modifications well known in the art, including heterocyclic derivatives and the like.

In preferred embodiments the modified ribozyme is a hammerhead, hairpin VS ribozyme or hepatitis delta virus derived ribozyme, and the hammerhead ribozyme includes between 32 and 40 nucleotide bases. The selection of modified bases is most preferably chosen to enhance the enzymatic activity (as observed in standard kinetic assays designed to measure the kinetics of cleavage) of the selected ribozyme, i.e., to enhance the rate or extent of cleavage of a substrate by the ribozyme, compared to a ribozyme having an identical nucleotide base sequence without any modified base.

By "enzymatic nucleic acid molecule" it is meant a nucleic acid molecule which has complementarity in a substrate binding region to a specified gene target, and also has an enzymatic activity which is active to specifically cleave RNA in that target. That is, the enzymatic nucleic acid molecule is able to inter-molecularly cleave RNA and thereby inactivate a target RNA molecule. This complementarity functions to allow sufficient hybridization of the enzymatic nucleic acid molecule to the target RNA to allow the cleavage to occur. One hundred percent complementarity is preferred, but complementarity as low as 50–75% may also be useful in this invention.

In preferred embodiments of this invention, the enzymatic nucleic acid molecule is formed in a hammerhead or hairpin motif, but may also be formed in the motif of a hepatitis delta virus, group I intron or RNaseP RNA (in association with an RNA guide sequence) or Neurospora VS RNA. Examples of such hammerhead motifs are described by Rossi et al., 1992, *Aids Research and Human Retroviruses* 8, 183, of hairpin motifs by Hampel et al., EP0360257, Hampel and Tritz, 1989 *Biochemistry* 28, 4929, and Hampel et al., 1990 *Nucleic Acids Res.* 18, 299, and an example of the hepatitis delta virus motif is described by Perrotta and Been, 1992 *Biochemistry* 31, 16; of the RNaseP motif by Guerrier-Takada et al., 1983 *Cell* 35, 849, Neurospora VS RNA ribozyme motif is described by Collins (Saville and Collins, 1990 *Cell* 61, 685–696; Saville and Collins, 1991 *Proc. Natl. Acad. Sci. USA* 88, 8826–8830; Collins and Olive, 1993 *Biochemistry* 32, 2795–2799) and of the Group I intron by Cech et al., U.S. Pat. No. 4,987,071. These specific motifs are not limiting in the invention and those skilled in the art will recognize that all that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule.

In a preferred embodiment the invention provides a method for producing a class of enzymatic cleaving agents which exhibit a high degree of specificity for the RNA of a desired target. The enzymatic nucleic acid molecule is preferably targeted to a highly conserved sequence region of a target RNAs such that specific treatment of a disease or condition can be provided with either one or several enzymatic nucleic acids. Such enzymatic nucleic acid molecules can be delivered exogenously to specific cells as required.

By "kinetic assays" or "kinetics of cleavage" is meant an experiment in which the rate of cleavage of target RNA is determined. Often a series of assays are performed in which the concentrations of either ribozyme or substrate are varied from one assay to the next in order to determine the influence of that parameter on the rate of cleavage.

By "rate of cleavage" is meant a measure of the amount of target RNA cleaved as a function of time.

In a second aspect, enzymatic nucleic acid having a hammerhead configuration and modified bases which maintain or enhance enzymatic activity is provided. Such nucleic acid is also generally more resistant to nucleases than unmodified nucleic acid. By "modified bases" in this aspect is meant those shown in FIG. 6 A–D, and 8, or their equivalents; such bases may be used within the catalytic core of the enzyme as well as in the substrate-binding regions. As noted above, substitution in the core may decrease in vitro activity but enhances stability. Thus, in vivo the activity may not be significantly lowered. As exemplified herein such ribozymes are useful in vivo even if active over all is reduced 10 fold. Such ribozymes herein are said to "maintain" the enzymatic activity on all RNA ribozyme.

Other features and advantages of the invention will be apparent from the following description of the preferred embodiments thereof, and from the claims.

DESCRIPTION OF THE PREFERRED EMBODIMENTS

The drawings will first briefly be described.

DRAWINGS

FIG. 1 is a diagrammatic representation of the hammerhead ribozyme domain known in the art. Stem II can be $\geq 2$ base-pair long. Each N is independently any base or non-nucleotide as used herein.

FIGS. 2A–2D are diagrammatic representation of the hammerhead ribozyme domain.

FIG. 2a is a diagrammatic representation of the hammerhead ribozyme domain known in the art; FIG. 2b is a diagrammatic representation of the hammerhead ribozyme as divided by Uhlenbeck (1987, *Nature,* 327, 596–600) into a substrate and enzyme portion; FIG. 2c is a similar diagram showing the hammerhead divided by Haseloff and Gerlach (1988, *Nature ,* 334, 585–591) into two portions; and FIG. 2d is a similar diagram showing the hammerhead divided by Jeffries and Symons (1989, *Nucl. Acids. Res.,* 17, 1371—1371) into two portions.

FIG. 3 is a diagrammatic representation of the general structure of a hairpin ribozyme. Helix 2 (H2) is provided with a least 4 base pairs (i.e., n is 1, 2, 3 or 4) and helix 5 can be optionally provided of length 2 or more bases (preferably 3–20 bases, i.e., m is from 1–20 or more). Helix 2 and helix 5 may be covalently linked by one or more bases (i.e., r is $\geq 1$ base). Helix 1, 4 or 5 may also be extended by 2 or more base pairs (e.g., 4–20 base pairs) to stabilize the ribozyme structure, and preferably is a protein binding site. In each instance, each N and N' independently is any normal or modified base and each dash represents a potential base-pairing interaction. These nucleotides may be modified at the sugar, base or phosphate. Complete base-pairing is not required in the helices, but is preferred. Helix 1 and 4 can be of any size (i.e., o and p is each independently from 0 to any number, e.g., 20) as long as some base-pairing is maintained. Essential bases are shown as specific bases in the structure, but those in the art will recognize that one or more may be modified chemically (abasic, base, sugar and/or phosphate modifications) or replaced with another base without significant effect. Helix 4 can be formed from two separate molecules, i.e., without a connecting loop. The connecting loop when present may be a ribonucleotide with or without modifications to its base, sugar or phosphate. "q" is ≧2 bases. The connecting loop can also be replaced with a non-nucleotide linker molecule. H, refers to bases A, U or C. Y refers to pyrimidine bases."

FIGS. 6a–d are diagrammatic representations of standard base modifications for adenine, guanine, cytosine and uracil, respectively.

Figure 7:
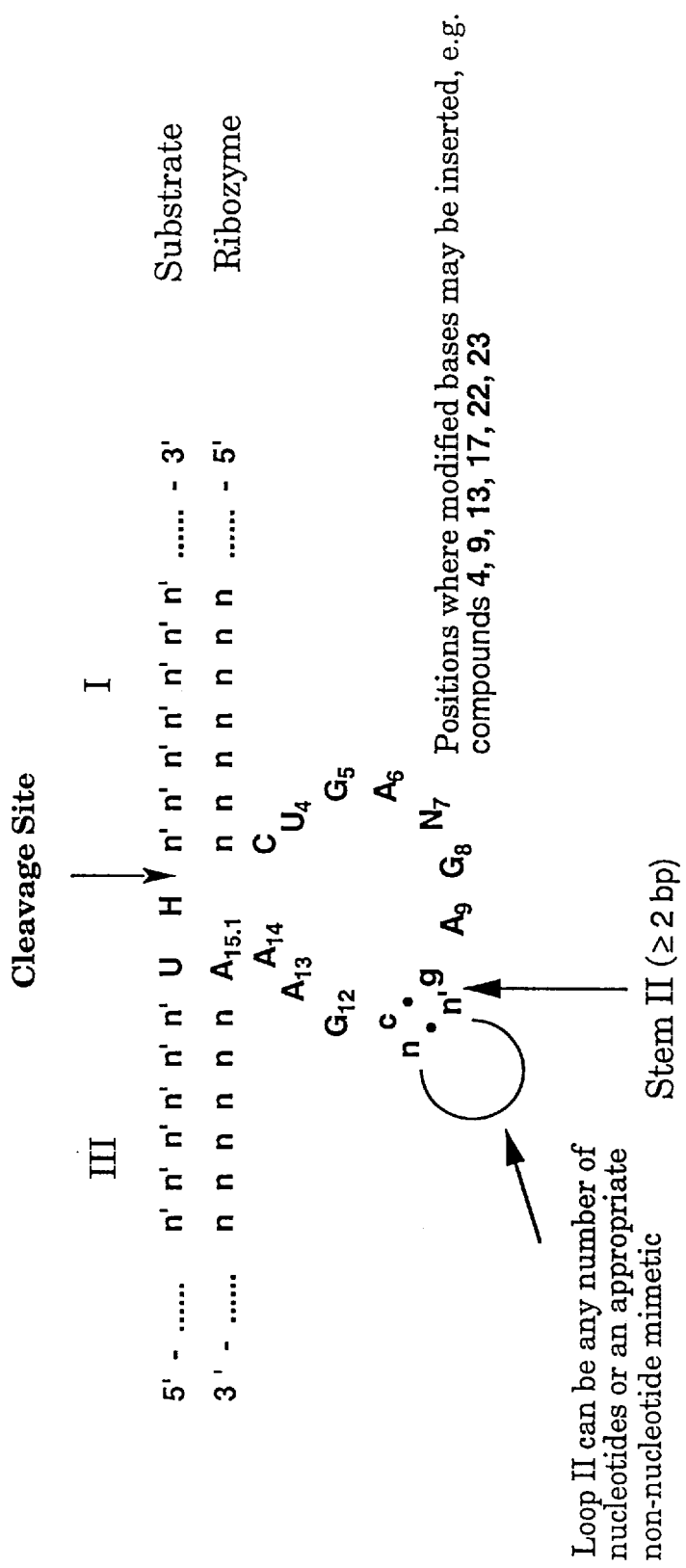

FIG. 7 is a diagrammatic representation of a position numbered hammerhead ribozyme (according to Hertel et al., *Nucleic Acids Res.* 1992, 20:3252) showing specific substitutions in the catalytic core and substrate binding arms. Compounds 4, 9, 13, 17, 22, 23 are described in FIG. 8.

FIG. 8 is a diagrammatic representation of various nucleotides that can be substituted in the catalytic core of a hammerhead ribozyme.

FIG. 9 is a diagrammatic representation of the synthesis of a ribothymidine phosphoramidite.

FIG. 10 is a diagrammatic representation of the synthesis of a 5-methylcytidine phosphoramidite.

FIG. 11 is a diagrammatic representation of the synthesis of 5-bromouridine phosphoramidite.

FIG. 12 is a diagrammatic representation of the synthesis of 6-azauridine phosphoramidite.

FIG. 13 is a diagrammatic representation of the synthesis of 2,6-diaminopurine phosphoramidite.

FIG. 14 is a diagrammatic representation of the synthesis of a 6-methyluridine phosphoramidite.

FIG. 15 is a representation of a hammerhead ribozyme targeted to site A (HHA). Site of 6-methyl U substitution is indicated.

Figure 16:
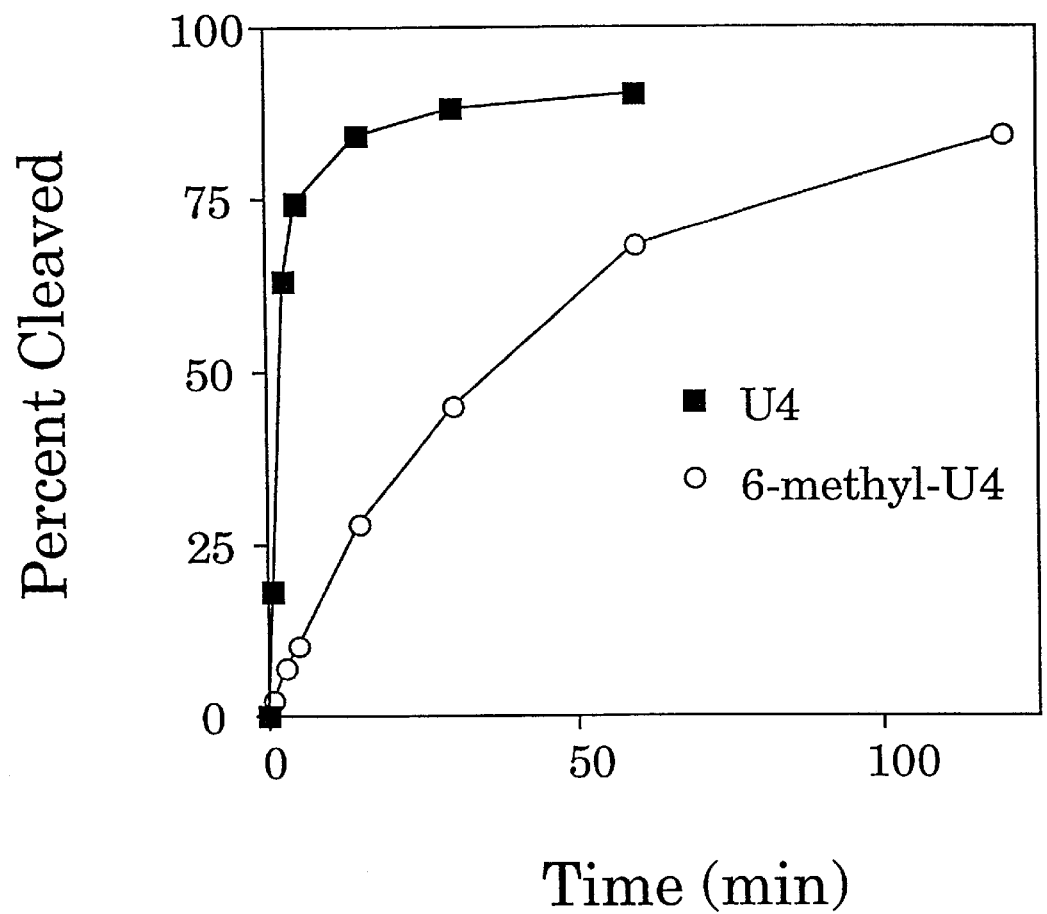

FIG. 16 shows RNA cleavage reaction catalyzed by HHA ribozyme containing 6-methyl U-substitution (6-methyl-U4). U4, represents a HHA ribozyme containing no 6-methyl-U substitution.

Figure 17:
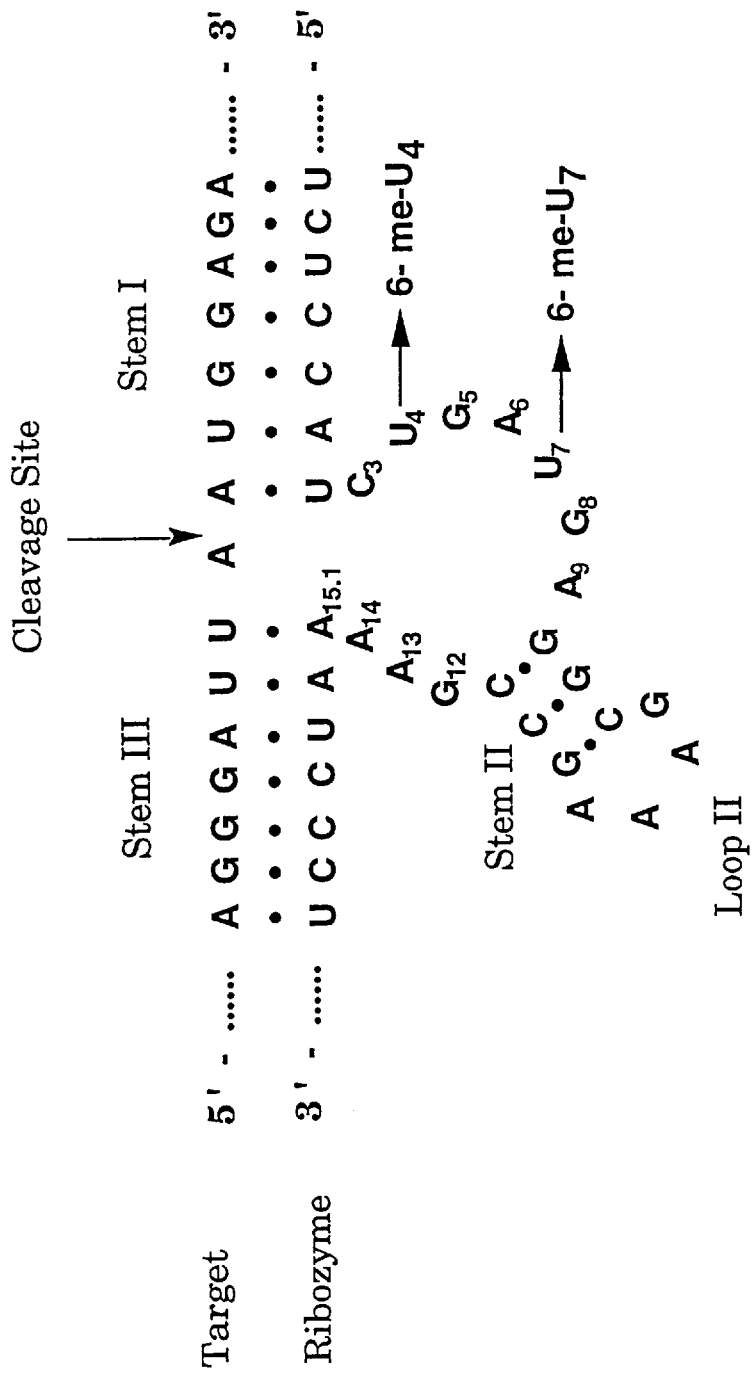

FIG. 17 is a representation of a hammerhead ribozyme targeted to site B (HHB). Sites of 6-methyl U substitution are indicated.

Figure 18:
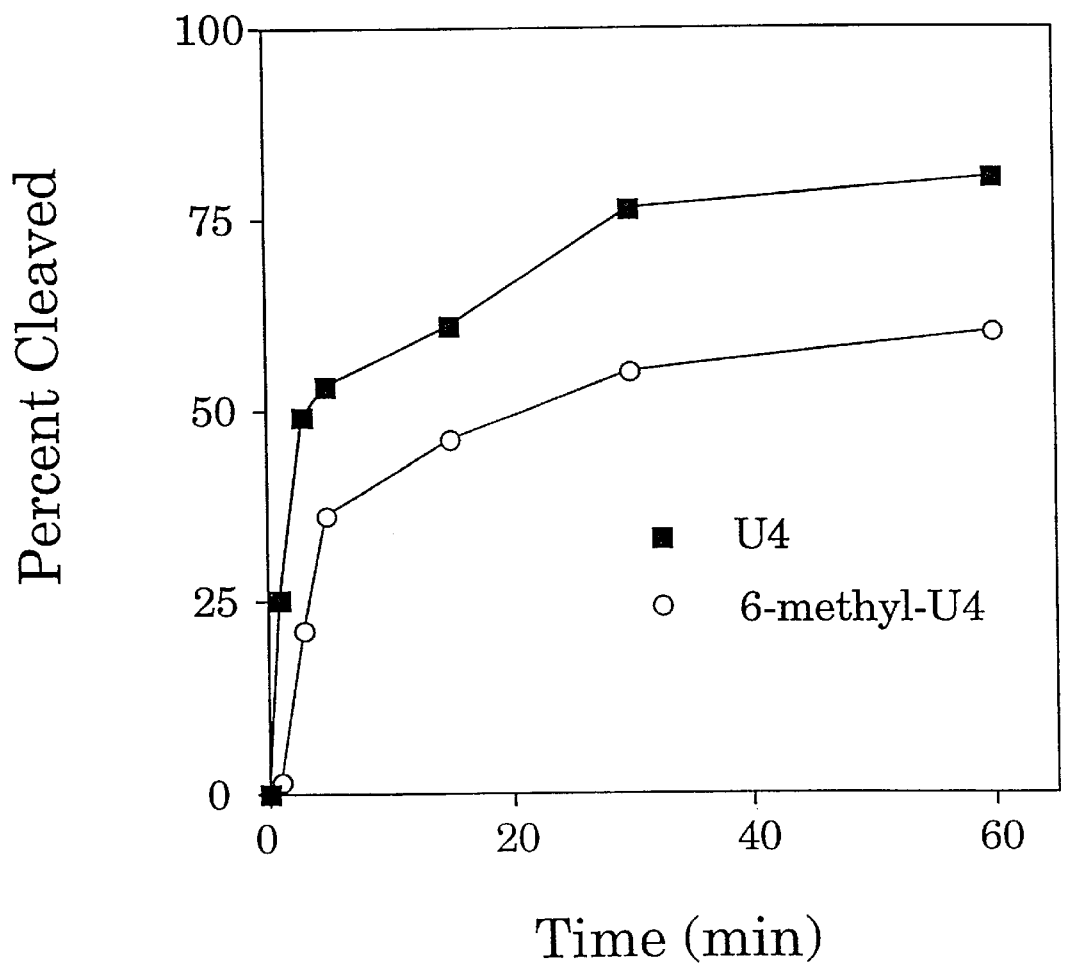

FIG. 18 shows RNA cleavage reaction catalyzed by HHB ribozyme containing 6-methyl U-substitutions at U4 and U7 positions (6-methyl-U4). U4, represents a HHB ribozyme containing no 6-methyl-U substitution.

Figure 19:
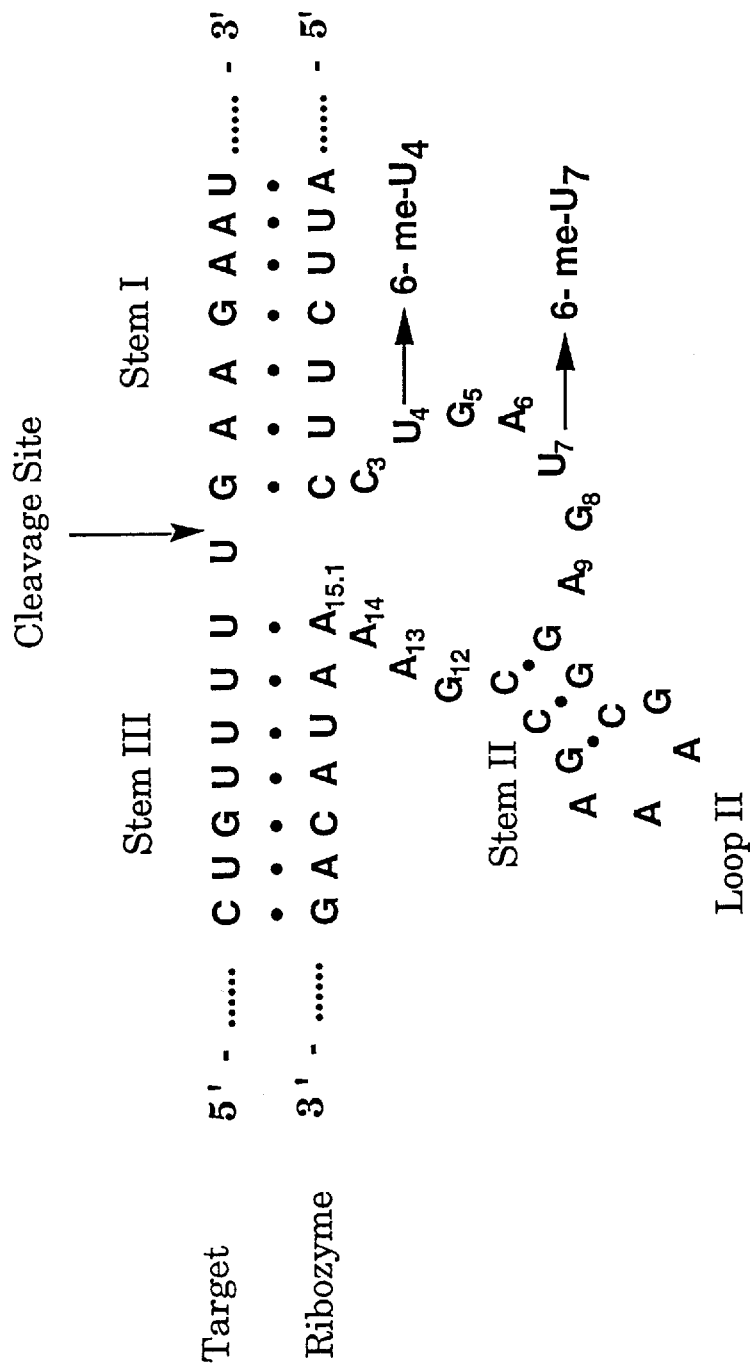

FIG. 19 is a representation of a hammerhead ribozyme targeted to site C (HHC). Sites of 6-methyl U substitution are indicated.

Figure 20:
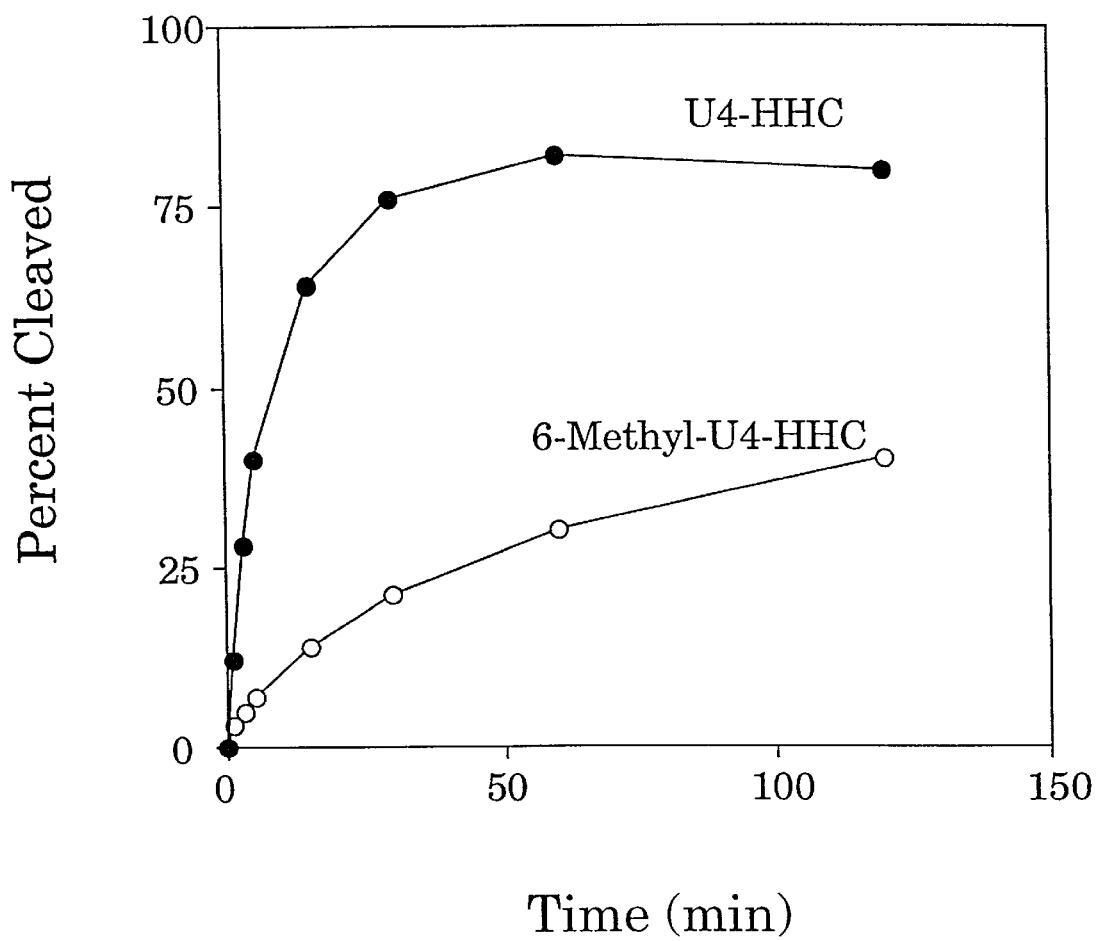

FIG. 20 shows RNA cleavage reaction catalyzed by HHC ribozyme containing 6-methyl U-substitutions at U4 and U7 positions (6-methyl-U4). U4, represents a HHC ribozyme containing no 6-methyl-U substitution.

Figure 21:
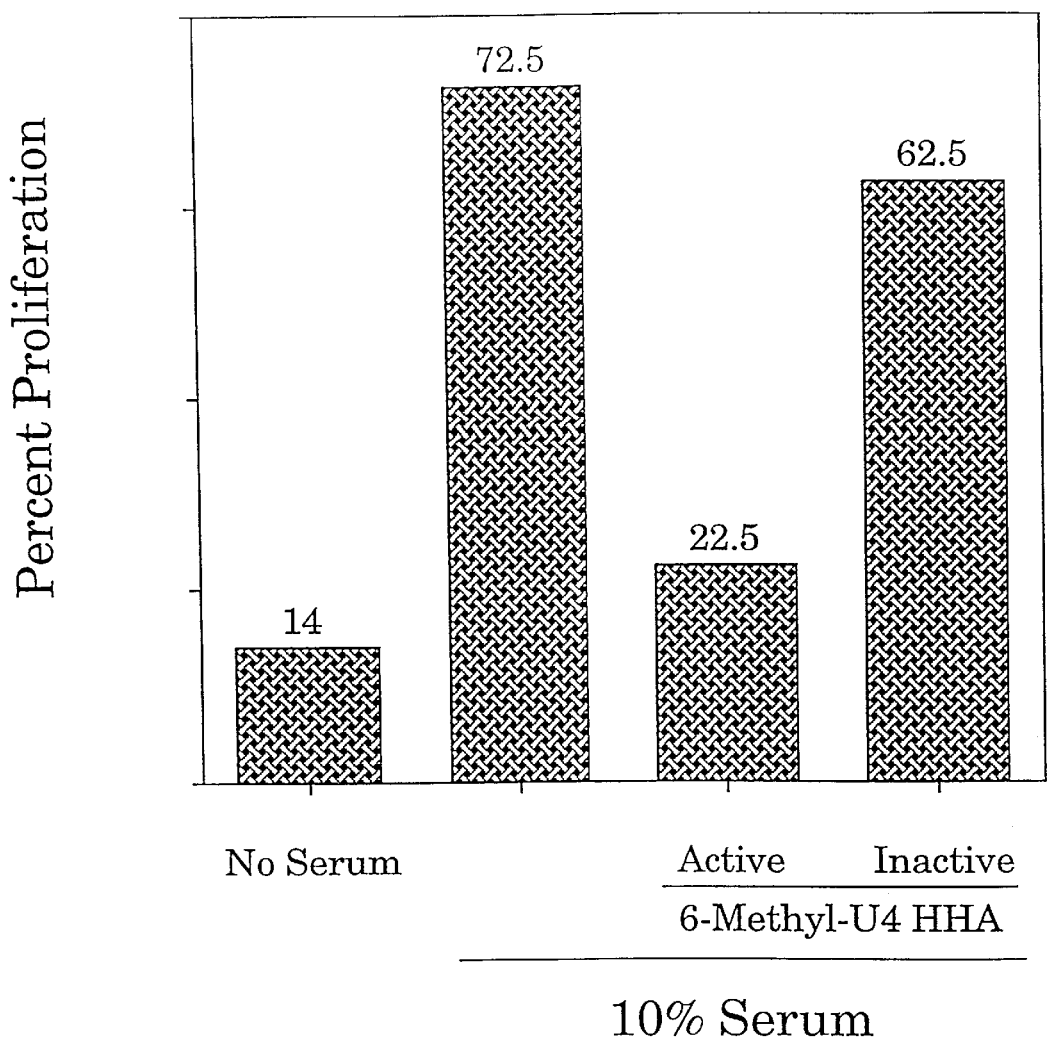

FIG. 21 shows 6-methyl-U-substituted HHA ribozyme-mediated inhibition of rat smooth muscle cell proliferation.

Figure 22:
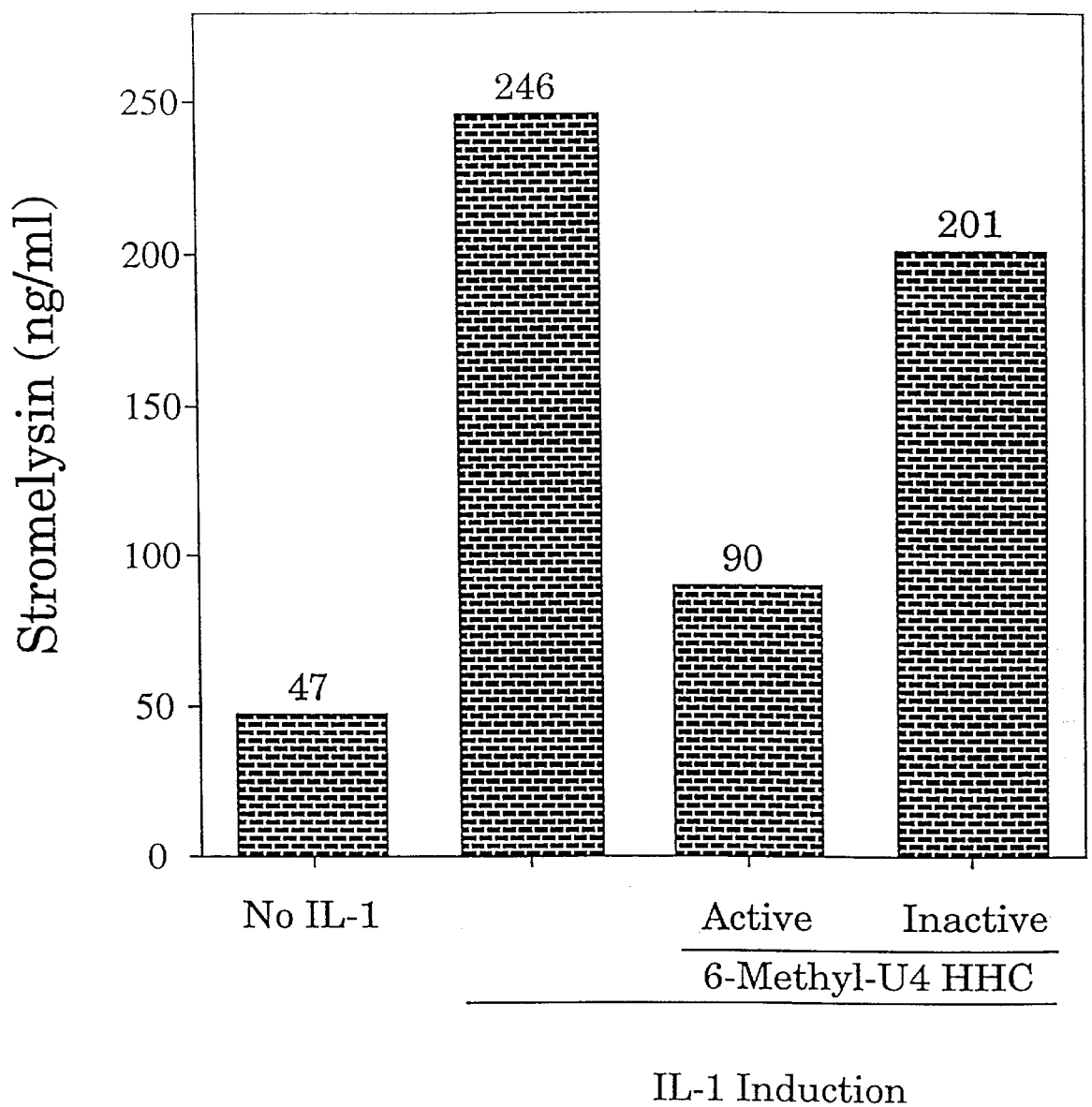

FIG. 22 shows 6-methyl-U-substituted HHC ribozyme-mediated inhibition of stromelysin protein production in human synovial fibroblast cells.

MODIFIED RIBOZYMES

There is a narrow range of binding free-energies between a ribozyme and its substrate that will produce maximal ribozyme activity. Such binding energy can be optimized by making ribozymes with G to I and U to BrU substitutions (or equivalent substitutions) in the substrate-binding arms. This allows manipulation of the binding free-energy without actually changing the target recognition sequence, the length of the two substrate-binding arms, or the enzymatic portion of the ribozyme. The shape of the free-energy vs. ribozyme activity curve can be readily determined using data from experiments in which each base (or several bases) is modified or unmodified, and without the complication of changing the size of the ribozyme/substrate interaction.

Such experiments will indicate the most active ribozyme structure. It is likely that only one or two modifications are necessary since a very small change in binding free energy (even one base-pair interaction) can dramatically affect ribozyme activity; the use of modified bases thus permits "fine tuning" of the binding free energy to assure maximal ribozyme activity. In addition, replacement of such bases, e.g., I for G, may permit a higher level of substrate specificity when cleavage of non-target RNA is a problem.

Method

Modified substrate binding arms can be synthesized using standard methodology. For example, phosphoramidites of inosine and 5-bromouracil can be used. Generally, a target site that has been optimized for stem I and III lengths (in a hammerhead ribozyme—other ribozymes can be treated in a similar manner), and that has G and/or U in the ribozyme portion of stem I and III, is selected. Modified ribozymes are made by replacing various G and U residues with I and BrU, respectively, during synthesis of the ribozyme. The modified ribozymes are then tested to determine kinetic parameters using standard procedures (see McSwiggen, "Improved Ribozymes", U.S. Ser. No. 07/884,521, filed May 14, 1992, hereby incorporated by reference herein). The binding affinities for the ribozymes can also be determined by standard procedures, e.g., by T-melt, gel-binding, or by competition kinetics assays. By comparison of binding affinity and ribozyme activity the optimum binding affinity of a ribozyme can then be found. Other combinations of G, I, U BrU, and other bases can then be tested with nearly identical binding free energy, but different base sequence, to determine whether factors other than simple binding free-energy play a role.

It is preferred to perform routine experiments of this type to select a desired ribozyme substrate binding sequence by use of an unmodified ribozyme with a modified substrate (which contains the modified bases). That is, the reverse experiment to that described above is performed. Such an experiment is more readily performed since the substrate is generally shorter than the ribozyme, and can be readily synthesized without concern about its secondary structure. Thus, a single ribozyme can be tested against a plurality of modified substrates in order to define which of the substrates provides better kinetic results. Once a preferred substrate is identified, the ribozyme can then be modified in a way which mirrors the selected substrate, and then tested against an unmodified substrate.

Such experiments will define useful ribozymes of this invention in which one or more modified bases are provided in the substrate binding arms with greater enzymatic activity in-vitro and in vivo than comparable unmodified ribozymes. Such modifications may also be advantageous if they increase the resistance of a ribozyme to enzymatic degradation in vivo.

Synthesis of Ribozymes

Synthesis of nucleic acids greater than 100 nucleotides in length is difficult using automated methods, and the therapeutic cost of such molecules is prohibitive. In this invention, small enzymatic nucleic acid motifs (e.g., of the hammerhead or the hairpin structure) are used for exogenous delivery. The simple structure of these molecules increases the ability of the enzymatic nucleic acid to invade targeted regions of the mRNA structure.

The ribozymes are chemically synthesized. The method of synthesis used follows the procedure for normal RNA synthesis as described in Usman et al., 1987 *J. Am. Chem. Soc.*, 109, 7845 and in Scaringe et al., 1990 *Nucleic Acids Res.*, 18, 5433 and makes use of common nucleic acid protecting and coupling groups, such as dimethoxytrityl at the 5'-end, and phosphoramidites at the 3'-end. The average stepwise coupling yields were >98%.

Ribozymes are purified by gel electrophoresis using general methods or are purified by high pressure liquid chromatography (HPLC; See Usman et al., Synthesis, deprotection, analysis and purification of RNA and ribozymes, filed May, 18, 1994, U.S. Ser. No. 08/245,736 the totality of which is hereby incorporated herein by reference) and are resuspended in water.

Various modifications to ribozyme structure can be made to enhance the utility of ribozymes. Such modifications will enhance shelf-life, half-life in vitro, stability, and ease of introduction of such ribozymes to the target site, e.g., to enhance penetration of cellular membranes, and confer the ability to recognize and bind to targeted cells.

Optimizing Ribozyme Activity

Ribozyme activity can be optimized as described by Stinchcomb et al., "Method and Composition for Treatment of Restenosis and Cancer Using Ribozymes," filed May 18, 1994, U.S. Ser. No. 08/245,466. The details will not be repeated here, but include altering the length of the ribozyme binding arms (stems I and III, see FIG. 2c), or chemically synthesizing ribozymes with modifications that prevent their degradation by serum ribonucleases (see e.g., Eckstein et al., International Publication No. WO 92/07065; Perrault et al., 1990 *Nature* 344, 565; Pieken et al., 1991 *Science* 253, 314; Usman and Cedergren, 1992 *Trends in Biochem. Sci.* 17, 334; Usman et al., International Publication No. WO 93/15187; and Rossi et al., International Publication No. WO 91/03162, as well as Usman, N. et al. U.S. patent application 07/829,729, and Sproat, European Patent Application 92110298.4 which describe various chemical modifications that can be made to the sugar moieties of enzymatic RNA molecules. Modifications which enhance their efficacy in cells, and removal of stem 11 bases to shorten RNA synthesis times and reduce chemical requirements. (All these publications are hereby incorporated by reference herein.).

Administration of Ribozyme

Sullivan et al., PCT WO94/02595, describes the general methods for delivery of enzymatic RNA molecules . Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination is locally delivered by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Sullivan et al., supra and Draper et al., PCT W093/23569 which have been incorporated by reference herein.

EXAMPLES

The following are non-limiting examples showing the synthesis of base-modified catalytic nucleic acids.

Example 1: Synthesis of Hammerhead Ribozymes Containing Base-Modified Nucleotides The method of synthesis used follows the procedure for normal RNA synthesis as de scribed in Usman et al., *J. Am. Chem. Soc.* 1987, 109, 7845–7854 and in Scaringe et al., *Nucleic Acids Res.* 1990, 18, 5433–5441 and makes use of common nucleic acid protecting and coupling groups, such as dimethoxytrityl at the 5'-end, and phosphoramidites at the 3'-end (compounds 4, 9, 13, 17, 22, 23). The average stepwise coupling yields were >98%. These base-modified nucleotides may be incorporated not only into hammerhead ribozymes, but also into hairpin, VS ribozymes, hepatitis delta virus, or Group 1 or Group 2 introns. They are, therefore, of general use as replacement motifs in any nucleic acid structure.

In the case of the hammerhead ribozyme the following specific substitutions may be used:

Referring to FIG. 7, in the catalytic core (numbered nucleotides), the pyrimidine C3 may be replaced by the cytosine analogs shown in FIG. 6c and compound 9 in FIG. 8.

Referring to FIG. 7, in the catalytic core (numbered nucleotides), the pyrimidines U4 and N7 may be replaced by the cytosine analogs shown in FIG. 4c, the uridine analogs shown in FIG. 6d and compounds 4,9,13 and 17 in FIG. 8 and FIG. 14.

Referring to FIG. 7, in the catalytic core (numbered nucleotides), the purines G5, G8 and G12 may be replaced by the guanine analogs shown in FIG. 6b and compounds 22 and 23 in FIG. 8.

Referring to FIG. 7, in the catalytic core (numbered nucleotides), the purines A6, A9, A13 and A14 may be replaced by the adenine analogs shown in FIG. 6a and compounds 22 and 23 in FIG. 8.

Figure 1:
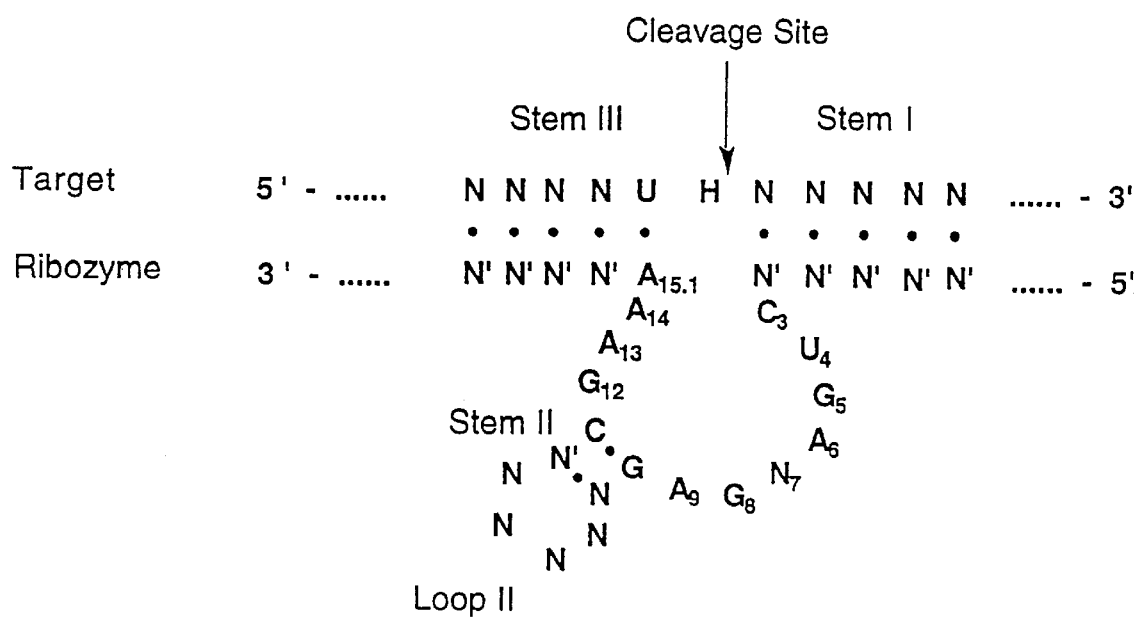
Figure 5:
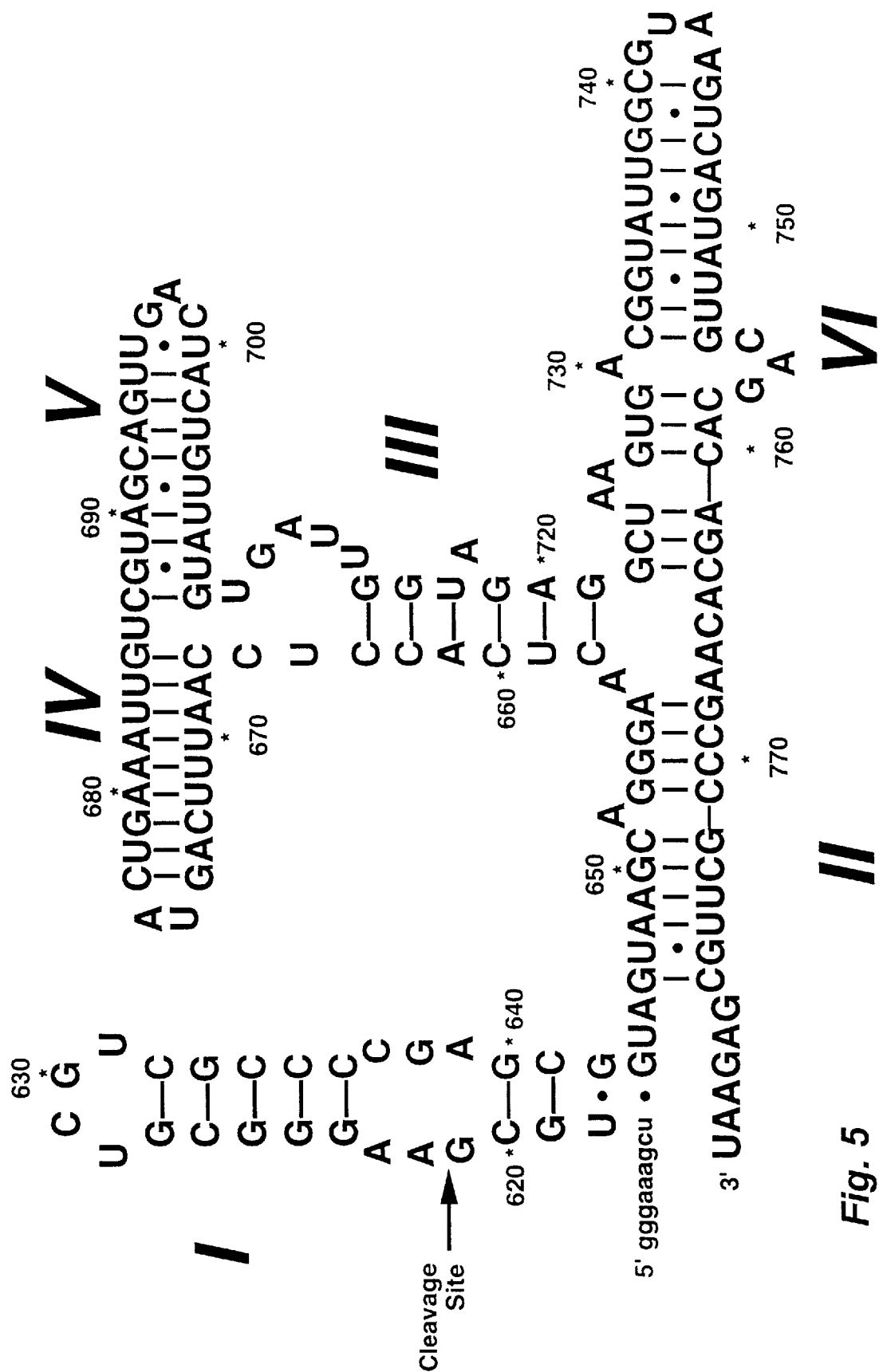
FIG. 5 is a representation of the general structure of the self-cleaving VS RNA ribozyme domain.

Referring to FIGS. 1 and 5, in stems I, II and III any of the pyrimidines may be replaced by the pyrimidine analogs shown in FIGS. 6c and 6d and compounds 4,9,13 and 17 in FIG. 8 and FIG. 14 as long as base-pairing is maintained in the stems.

Figure 2:
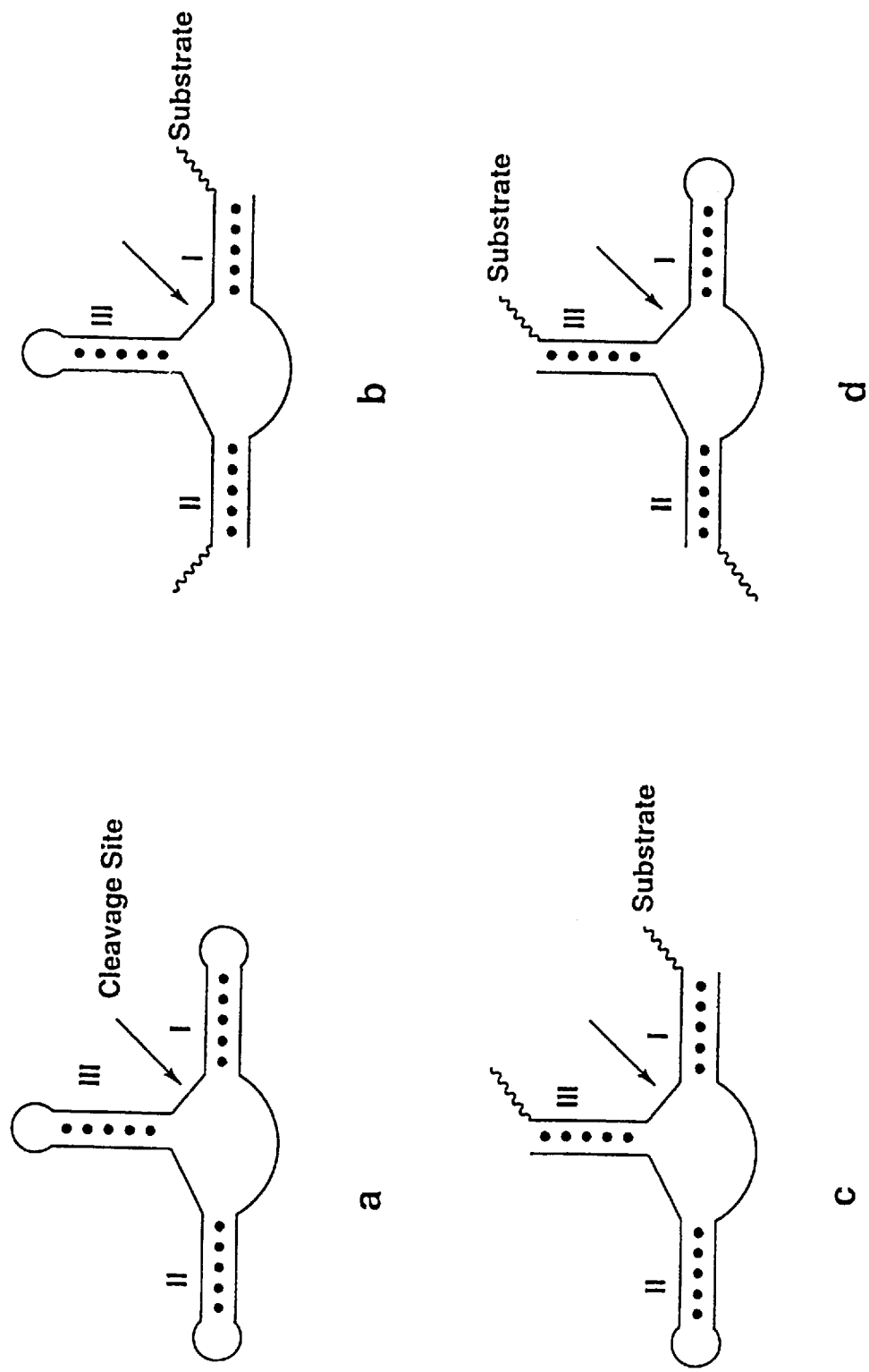

Referring to FIGS. 1 2 and 7, in stems I, II and III any of the purines may be replaced by the purine analogs shown in FIGS. 6a and 6b and compounds 22 and 23 in FIG. 8 as long as base-pairing is maintained in the stems.

Referring to FIGS. 1 2 and 7, in loop II (denoted as loop II in FIG. 7) any nucleotide may be replaced by the pyrimidine analogs shown in FIGS. 6c and 6d, the purine analogs shown in FIGS. 6a and 6b and compounds 4,9,13, 17, 22 and 23 in FIG. 8 and FIG. 14.

Example 2: Synthesis of Ribothymidine Phosphoramidite 4

Referring to FIG. 9, ribothymidine 1 was prepared according to Vorbruggen et al., *Chem. Ber.* 1981, 114:1234, and tritylated to yield DMT derivative 2. 2 was silylated to yield 2'-O-TBDMS derivative 3. The phosphoramidite 4 was prepared according to Scaringe et al., *Nucleic Acids Res.* 1990, 18:5433.

Example 3: Synthesis of 5-Methylcytidine Phosphoramidite 9

Referring to FIG. 10, Ribothymidine 1 (4 g, 15.5 mmol) was coevaporated with dry pyridine (2×100 ml) and redissolved in dry pyridine (100 ml). To the resulting solution 4,4'-DMT-Cl (6.3 g, 18.6 mmol) was added and the reaction mixture was left at room temperature (about 20°–25° C. for 16 hours. The reaction mixture was quenched with methanol (25 ml) and evaporated to dryness. The residue was partitioned between chloroform and 5% sodium bicarbonate. The organic layer was washed with 5% sodium bicarbonate and brine, then dried over sodium sulfate and evaporated. The residue was additionally dried by coevaporation with dry pyridine (2×50 ml) then redissolved in dry pyridine (100 ml) and acetic anhydride (4.4 ml, 46.5 mmol) was added to the resulting solution. The reaction mixture was left at room temperature overnight, then quenched with methanol (25 ml), evaporated and worked-up as outlined above. The crude 5'-O-dimethoxytrityl-2',3',-di-O-acetyl-ribo-thymidine 5 was purified by flash chromatography on silica gel, (hexanes:ethylacetate:triethylamine/45:45:10 to give 6.86 g (68.7%) of 5 as a yellowish foam.

Triethylamine (14.72 ml, 105.6 mmol) was added dropwise to a stirred ice-cooled mixture of triazole (6.56 g, 95.04 mmol) and phosphorous oxychloride (2 ml, 21.2 mmol) in 100 ml of dry acetonitrile. A solution of nucleoside 5 (6.89, 10.56 mmol) in 50 ml. of dry acetonitrile was added dropwise to the resulting suspension and the reaction mixture was stirred at room temperature for 4 hours. The reaction was concentrated, dissolved in chloroform and washed with a saturated aqueous solution of sodium bicarbonate, water, dried over sodium sulfate and evaporated to dryness. To a solution of the residue (7.24 g) in dioxane (120 ml) was added 40 ml of 29% aqueous $NH_4OH$ and the resulting solution was left overnight, then evaporated to dryness to yield 6.86 g of crude cytidine derivative 6 which was used without purification.

To a solution of 6 (3.5 g, 6.25 mmol) in dry pyridine (100 ml) was added 3.97 ml of trimethylchlorosilane to transiently protect free sugar hydroxyls. The reaction mixture was then treated with isobutyryl chloride (0.98 ml, 9.375 mmol) for 5 hours. The resulting mixture was quenched with 10 ml of methanol, then 10 ml of water was added and after 10 minutes 10 ml of 29% aq. ammonia was added and the reaction mixture was stirred for 2 hours and evaporated to dryness. The resulting residue was worked-up as outlined above for the compound 5 and purified by flash chromatography on silica gel (ethylacetate:hexanes/1:3) to yield 2.37 g (60%) of the nucleoside 7.

To a solution of compound 7 (1.3 g, 2.06 mmol) in dry pyridine 0.97 g (5.72 mmol) of silver nitrate was added followed by 2.86 ml of a 1M solution of tert-butyldimethyl chloride in THF. The reaction mixture was left for 8 hours, evaporated, and dissolved in chloroform. The silver salt precipitate was filtered off and the reaction solution was washed with 5% aq. sodium bicarbonate and brine, dried over sodium sulfate and evaporated. The mixture of 2'- and 3'-isomers was separated by flash chromatography on silica gel (hexanes:ethylacetate/4:1) to yield 0.62 g (40%) of 2'-isomer 8, which was converted to the phosphoramidite 9 by the general method described in Scaringe et al., *Nucleic Acids Res.* 1990, 18:5433.

Example 4: Synthesis of 5-Bromouridine Phosphoramidite13 (See, Talbat et al., *Nucl. Acids Res.* 18:3521—21, 1990)

Referring to FIG. 11, 5-Bromouridine 10 (1.615 g, 5 mmol) was coevaporated with dry pyridine and redissolved in dry pyridine. To the resulting solution 2.03 g (6 mmol) of DMT-Cl was added and the reaction mixture was left overnight. After work-up and purification by flash chromatography on silica gel (chloroform:methanol/95:5) 2.5 g (80%) of the dimethoxytritylated compound 11 was obtained.

To a solution of 11 (2 g) in dry pyridine was added 1.5 eq. of TBDMS-Cl for 2 days. The reaction mixture was evaporated, dissolved in chloroform, washed with 5% aq. sodium bicarbonate and brine. The organic layer was dried over sodium sulfate, evaporated and purified by flash chromatography on silica gel (ethylacetate:hexanes/1:2) to yield 1.4 g (60%) of 2'-isomer 12, which was converted to the phosphoramidite 13 by the general method described in Scaringe et al., *Nucleic Acids Res.* 1990, 18:5433.

Example 5: Synthesis of 6-azauridine Phosphoramidite 17

Referring to FIG. 12, 6-Azauridine (4.9 g, 20 mmol) was evaporated with dry pyridine (2×100 ml) and dissolved in dry pyridine (100 ml) and, after addition of 4,4'-DMT-Cl (7.45 g, 22 mmol) left for 16 hours at room temperature. The reaction mixture was diluted with dry MeOH (50 ml), evaporated to dryness, coevaporated with toluene (2×100 ml), the residue dissolved in $CHCl_3$ (500 ml) and washed with 5% $NaHCO_3$ (100 ml), brine (100 ml), dried, and purified by flash chromatography (a gradient $CHCl_3$ to 5% $EtOH/CHCl_3$ to yield 1 g (92.2%) of intermediate) 15.

To a solution of 15 (3.23 g, 5.9 mmol) in 100 ml of dry THF, $AgNO_3$ (7.08 mmol) and dry pyridine (2.1 ml, 4.4 mmol) were added. The reaction mixture was stirred at room temperature until full dissolution of $AgNO_3$ (about 1 hour) occurred. Then 7 ml of a 1M solution of TBDMS-Cl in THF was added and the reaction mixture stirred for 16 hours at room temperature. The reaction mixture was filtered and the filtrate evaporated to dryness. The resulting residue was dissolved in $CHCl_3$ (300 ml) and washed with 5% $NaHCO_3$ (100 ml), brine (100 ml), dried, and purified by flash chromatography (gradient of hexanes to hexanes:ethyl acetate/ 1:1) to yield 3.71 g (62%) of 2'-TBDMS-isomer 16 which was converted to the phosphoramidite 17 by the general method described in Scaringe et al., *Nucleic Acids Res.* 1990, 18:5433.

Example 6: Synthesis of 2.6-diaminopurine Phosphoramidite 22

Referring to FIG. 13, phosphoramidite 22 was prepared by the general method described in Scaringe et al., *Nucleic Acids Res.* 1990, 18:5433. Specifically, guanosine (11.32 g, 40 mmol) was dried by coevaporation with dry pyridine and redissolved in dry pyridine. Chlorotrimethylsilane (26.4 ml, 208 mmol) was added under stirring to the above solution and the reaction mixture was stirred overnight. To the resulting persilylated guanosine derivative phenylacetylchloride (12.7 ml, 96 mmol) was added dropwise and the reaction mixture was stirred for 12 hours. The reaction was quenched with 50 ml of methanol and 50 ml of water and stirred for 15 minutes, then 50 ml of 29% ammonia was added and the reaction mixture left for an additional 2 hours. Solvents were removed in vacuo, and the resulting oil was partitioned between ethyl acetate and water. The separated water layer was washed with ethyl acetate and was precipitated at 4° C. The resulting solid was filtered off to give 8 g of N$^2$phenylacetylguanosine 18. The mother liquor was concentrated to give additional crop (4 g). Overall yield ~12 g (75%).

N$^2$Phenylacetylguanosine 18 (2.3 g, 5.73 mmol) was dried by coevaporation (3 times) with dry pyridine and dissolved in 50 ml of dry pyridine. To the resulting solution dimethoxytritylchloride (2.33 g, 6.88 mmol) was added and the reaction mixture was left at room temperature for 5 hours. The reaction was quenched with 25 ml of methanol and evaporated to dryness. The residue was dissolved in dichloromethane, washed with 5% aq. sodium bicarbonate and brine, dried over sodium sulfate and evaporated. The resulting oil was further dried by coevaporation with dry pyridine, dissolved in pyridine and treated with acetic anhydride (1.4 ml) for 4 hours at room temperature. The reaction mixture was quenched and worked-up as described above. The crude final compound was purified by flash chromatography on silica gel using dichloromethane:methanol/98:2 mixture as eluent. The desired fractions were collected and evaporated to give 3.5 g (77%) of 5'-O-dimethoxytrityl-2', 3'-di-O-acetyl-N$^2$-phenylacetylguanosin e 19 as a yellowish foam.

To a solution of compound 19 (3.5 g, 4.45 mmol) in 50 ml of dry dichloromethane, containing 3.11 ml of diisopropylethylamine, was added mesitylenesulfonyl chloride (1.9 g, 8.9 mmol) and dimethylaminopyridine (0.28 g). The reaction mixture was stirred for 30 minutes, evaporated and purified by flash chromatography on silica gel using dichloromethane (1 l) followed by 2% Methanol in dichloromethane (0.7 l) to give 2.8 g (64%) of O$^6$-mesitylene intermediate 20. To a solution of 20 in 40 ml of dry tetrahydrofuran lithium disulfide (0.3 g, 6.8 mmol) was added and the reaction mixture was stirred for 20 hours. The resulting clear solution was evaporated and worked-up as described above. The residue was purified by flash chromatography on silica gel in 1% Methanol in dichloromethane to give 1.1 g (31%) of 5'-O-dimethoxytrityl-2',3'-di-O-acetyl-N$^2$phenylacetyl-6-thiogua nosine 21.

To an ice-cooled (0° C.) solution of 5'-O-dimethoxytrityl-2',3'-di-O-acetyl-N$^2$phenylacetyl-6-thiogua nosine 21 (1 g) in pyridine:methanol/20 ml:2.6 ml, 2.4 ml of 1M aq. sodium hydroxide were added and the reaction mixture was allowed to stay at 0° C. for 20 minutes. The solution was neutralized with Dowex 2×8 (Pyr$^+$) to pH 7. The resin was filtered off and washed with aq. pyridine. The combined filtrate and washings were evaporated and dried in vacuo to give quantitatively 5'-O-dimethoxytrityl-N$^2$phenylacetyl-6-thioguanosine.

To a stirred suspension of 5'-O-dimethoxytrityl-N$^2$phenylacetyl-6-thioguanosine (1.13 g, 1.57 mmol) in dry acetonitrile (35 ml) and triethylamine (1 ml) was added dinitrofluorobenzene (0.34 g, 1.88 mmol) and the reaction mixture was stirred under anhydrous conditions for 2 hours. The reaction was evaporated and worked-up as described for compound 20 and purified by flash chromatography on silica gel in 1% methanol in chloroform (containing 1 % triethylamine) as an eluent to give 0.93 g (67%) of 5'-O-dimethoxytrityl-N$^2$phenylacetyl-6-S-dinitrophenyl guanosine.

To a solution of 5'-O-dimethoxytrityl-N$^2$phenylacetyl-6-S-dinitrophenyl guanosine (0.9 g,1 mmol) in dry pyridine t-butyldimethylsilylchloride (0.46 g, 3 mmol) and tetrabutylammonium nitrate (3 mmol) were added and the reaction mixture was left for 50 hours. TLC (hexane:ethyl acetate/ 3:1) showed disappearance of the starting material and formation of two new compounds with a predominance of a lower R$_f$ (3'-O-silyl isomer according to $^1$H-NMR). The desired 2'-isomer (70 mg) was obtained after evaporation and work-up and separation by flash chromatography on silica gel using hexane:ethyl acetate/4:1 as eluent. The remaining mixture was rearranged in methanol with 2 drops of triethylamine and separated as above. This rearrangement procedure was repeated twice to finally give 250 mg of the desired 2'-isomer. 5'-O-dimethoxytrityl-2'-O-t-butyldimethylsilyl-N$^2$phenylacetyl-6-S-dinitrophenyl guanosine.

5'-O-Dimethoxytrityl-2'-O-t-butyldimethylsilyl-N$^2$phenylacetyl-6-S-dinitrophenyl guanosine (0.18 g, 0.18 mmol) was dissolved in dry tetrahydrofuran under dry argon. N-Methylimidazole (0.01 ml, 0.09 mmol) and sym-collidine (0.178 ml, 1.35 mmol) were added and the solution was ice-cooled. 2-Cyanoethyl N,N'-diisopropylchlorophosphoramidite (0.083 ml, 0.36 mmol) was added dropwise and stirring was continued for 3 hours at room temperature. The reaction mixture was again ice-cooled and quenched with 6 ml of dry degassed ethyl acetate. After 5 min stirring the mixture was concentrated in vacuo (40° C.), dissolved in chloroform, washed with 5% aq sodium bicarbonate, then with brine and evaporated. The residue was purified by flash chromatography on silica gel using ethyl acetate:hexane/:3 containing 2% triethylamine as an eluent to yield 0.14 g (64%) 5'-O-dimethoxytrityl-2'-O-t-butyldimethylsilyl-N$^2$phenylacetyl-6-S-dinitrophenylguanosine- 3'-(2-cyanoethyl N,N-diisopropylphosphoramidite) 22 as a yellow foam.

Example 7: Synthesis of 6-methyl-uridine phosphoramidite

Referring to FIG. 14, the suspension of 6-methyl-uracil (2.77g, 21.96 mmol) in the mixture of hexamethyidisilazane (5 mL) and dry pyridine (5 mL) was refluxed for three hours. The resulting clear solution of trimethylsilyl derivative of 6-methyl uracyl was evaporated to dryness and coevaporated 2 times with dry toluene to remove traces of pyridine. To the solution of the resulting clear oil, in dry acetonitrile, 1-O-acetyl-2',3',5'-tri-O-benzoyl-b-D-ribose (10.1 g, 20 mmol) was added and the reaction mixture was cooled to 0° C. To the above stirred solution, trimethylsilyl trifluoromethanesulfonate (4.35 mL, 24 mmol) was added dropwise and the reaction mixture was stirred for 1.5 h at 0° C. and then 1 h at room temperature. After that the reaction mixture was diluted with dichloromethane washed with saturated sodium bicarbonate and brine. The organic layer was evaporated and the residue was purified by flash chromatography on silica gel with ethylacetate-hexane (2:1) mixture as an eluent to give 9.5 g (83%) of the compound 2 and 0.8 g of the corresponding N$^1$, N$^3$-bis-derivative.

To the cooled (−10° C.) solution of the compound (4.2 g, 7.36 mmol) in the mixture of pyridine (60 mL) and methanol (10 mL) ice-cooled 2M aqueous solution of sodium hydroxide (16 mL) was added with constant stirring. The reaction mixture was stirred at −10° C. for additional 30 minutes and then neutralized to pH 7 with Dowex 50 (Py$^+$). The resin was filtered off and washed with a 200 mL mixture of H$_2$O - Pyridine (4:1). The combined "mother liquor" and the washings were evaporated to dryness and dried by multiple coevaporation with dry pyridine. The residue was redissolved in dry pyridine and then mixed with dimethoxytrityl chloride (2.99 g, 8.03 mmol). The reaction mixture was left overnight at room temperature. Reaction was quenched with methanol (25 mL) and the mixture was evaporated. The residue was dissolved in dichloromethane, washed with saturated aqueous sodium bicarbonate and brine. The organic layer was dried over sodium sulfate and evaporated. The residue was purified by flash chromatography on silica gel using linear gradient of MeOH (2% to 5%) in CH$_2$Cl$_2$ as eluent to give 3.4 g (83%) of the compound 6.

Example 8: Synthesis of 6-methyl-cytidine phosphoramidite

Triethylamine (13.4 ml, 100 mmol) was added dropwise to a stirred ice-cooled mixture of 1,2,4-triazole (6.22 g, 90 mmol) and phosphorous oxychloride (1.89 ml, 20 mmol) in 50 ml of anhydrous acetonitrile. To the resulting suspension the solution of 2',3',5'-tri-O-Benzoyl-6-methyl uridine (5.7 g, 10 mmol) in 30 ml of acetonitrile was added dropwise and the reaction mixture was stirred for 4 hours at room temperature. Then it was concentrated in vacuo to minimal volume (not to dryness). The residue was dissolved in chloroform and washed with water, saturated aq sodium bicarbonate and brine. The organic layer was dried over sodium sulfate and the solvent was removed in vacuo. The residue was dissolved in 100 ml of 1,4-dioxane and treated with 50 mL of 29% aq NH$_4$OH overnight. The solvents were removed in vacuo. The residue was dissolved in the in the mixture of pyridine (60 mL) and methanol (10 mL), cooled to –15° C. and ice-cooled 2M aq solution of sodium hydroxide was added under stirring. The reaction mixture was stirred at –10° to –15° C. for additional 30 minutes and then neutralized to pH 7 with Dowex 50 (Py$^+$). The resin was filtered off and washed with 200 mL of the mixture H$_2$O - Py (4:1). The combined mother liquor and washings were evaporated to dryness. The residue was cristallized from aq methanol to give 1.6 g (62%) of 6-methyl cytidine.

To the solution of 6-methyl cytidine (1.4g, 5.44 mmol) in dry pyridine 3.11 mL of trimethylchlorosilane was added and the reaction mixture was stirred for 2 hours at room temperature. Then acetic anhydride (0.51 mL, 5.44 mmol) was added and the reaction mixture was stirred for additional 3 hours at room temperature. TLC showed disappearance of the starting material and the reaction was quenched with MeOH (20 mL), ice-cooled and treated with water (20 mL, 1 hour). The solvents wee removed in vacuo and the residue was dried by four coevaporations with dry pyridine. Finally it was redissolved in dry pyridine and dimethoxytrityl chloride (2.2 g, 6.52 mmol) was added. The reaction mixture was stirred overnight at room temperature and quenched with MeOH (20 mL). The solvents were removed in vacuo. The remaining oil was dissolved in methylene chloride, washed with saturated sodium bicarbonate and brine. The organic layer was separated and evaporated and the residue was purified by flash chromatography on silica gel with the gradient of MeOH in methylene chloride (3% to 5%) to give 2.4 g (74%) of the compound (4).

Example 9: Synthesis of 6-aza-uridine and 6-aza-cytidine

To the solution of 6-aza uridine (5 g, 20.39 mmol) in dry pyridine dimethoxytrityl chloride (8.29 g, 24.47 mmol) was added and the reaction mixture was left overnight at room temperature. Then it was quenched with methanol (50 mL) and the solvents were removed in vacuo. The remaining oil was dissolved in methylene chloride and washed with saturated aq sodium bicarbonate and brine. The organic layer was separated and evaporated to dryness. The residue was additionally dried by multiple coevaporations with dry pyridine and finally dissolved in dry pyridine. Acetic anhydride (4.43 mL, 46.7 mmol) was added to the above solution and the reaction mixture was left for 3 hours at room temperature. Then it was quenched with methanol and worked-up as above. The residue was purified by flash chromatography on silics gel using mixture of 2% of MeOH in methylene chloride as an eluent to give 9.6 g (75%) of the compound.

Triethylamine (23.7 ml, 170.4 mmol) was added dropwise to a stirred ice-cooled mixture of 1,2,4-triazole (10.6 g, 153.36 mmol) and phosphorous oxychloride (3.22 ml, 34.08 mmol) in 100 ml of anhydrous acetonitrile. To the resulting suspension the solution of 2',3'-di-O-Acetyl-5'-O-Dimethoxytrityl-6-aza Uridine (7.13 g, 11.36 mmol) in 40 ml of acetonitrile was added dropwise and the reaction mixture was stirred for 6 hours at room temperature. Then it was concentrated in vacuo to minimal volume (not to dryness). The residue was dissolved in chloroform and washed with water, saturated aq sodium bicarbonate and brine. The organic layer was dried over sodium sulfate and the solvent was removed in vacuo. The residue was dissolved in 150 ml of 1,4-dioxane and treated with 50 mL of 29% aq NH$_4$OH for 20 hours at room temperature. The solvents were removed in vacuo. The residue was purified by flash chromatigraphy on silica gel using linear gradient of MeOH (4% to 10%) in methylene chloride as an eluent to give 3.1 g (50%) of azacytidine.

To the stirred solution of 5'-O-Dimethoxytrityl-6-aza cytidine (3g, 5.53 mmol) in anhydrous pyridine trimethylchloro silane (2.41 mL, 19 mmol) was added and the reaction mixture was left for 4 hours at room temperature. Then acetic anhydride (0.63 mL, 6.64 mmol) was added and the reaction mixture was stirred for additional 3 hours at room temperature. After that it was quenched with MeOH (15 mL) and the solvents were removed in vacuo. The residue was treated with 1M solution of tetrabutylammonium fluoride in THF (20°, 30 min) and evaporated to dryness. The remaining oil was dissolved in methylene chloride, washed with saturated aq sodium bicarbonate and water. The separated organic layer aws dried over sodium sulfate and evaporated to dryness. The residue was purified by flash chromatography on silica gel using 4% MeOH in methylene chloride as an eluent to give 2.9 g (89.8%) of the compound.

General Procedure for the Introducing of the TBDMS-Group: To the stirred solution of the protected nucleoside in 50 mL of dry THF and pyridine (4 eq) AgNO$_3$ (2.4 eq) was added. After 10 minutes tert-butyldimethylsilyl chloride (1.5 eq) was added and the reaction mixture was stirred at room temperature for 12 hours. The resulted suspension was filtered into 100 mL of 5% aq NaHCO$_3$. The solution was extracted with dichloromethane (2×100 mL). The combined organic layer was washed with brine, dried over Na$_2$SO$_4$ and evaporated. The residue was purified by flash chromatography on silica gel with hexanes-ethylacetate (3:2) mixture as eluent.

General Procedure for Phosphitylation: To the ice-cooled stirred solution of protected nucleoside (1 mmol) in dry dichloromethane (20 mL) under argon blanket was added dropwise via syringe the premixed solution of N,N-diisopropylethylamine (2.5 eq) and 2-cyanoethyl N'N-diisopropylchlorophosphoramidite (1.2 eq) in dichloromethane (3 mL). Simultaneously via another syringe N-methylimidazole (1 eq) was added and stirring was continued for 2 hours at room temperature. After that the reaction mixture was again ice-cooled and quenched with 15 ml of dry methanol. After 5 min stirring, the mixture was concentrated in vacuo (<40° C.) and purified by flash chromatography on silica gel using hexanes-ethylacetate mixture contained 1% triethylamine as an eluent to give corresponding phosphoroamidite as white foam.

Example 10: RNA cleavage activity of HHA ribozyme substituted with 6-methyl-Uridine Hammerhead ribozymes targeted to site A (see FIG. 15) were synthesized using solid-phase synthesis, as described above. U4 position was modified with 6-methyl-uridine.
RNA cleavage assay in vitro:

Substrate RNA is 5'end-labeled using $[\gamma^{-32}P]$ ATP and T4 polynucleotide kinase (US Biochemicals). Cleavage reactions were carried out under ribozyme "excess" conditions. Trace amount ($\leq 1$ nM) of 5' end-labeled substrate and 40 nM unlabeled ribozyme are denatured and renatured separately by heating to 90° C. for 2 min and snap-cooling on ice for 10–15 min. The ribozyme and substrate are incubated, separately, at 37° C. for 10 min in a buffer containing 50 mM Tris-HCl and 10 mM $MgCl_2$. The reaction is initiated by mixing the ribozyme and substrate solutions and incubating at 37° C. Aliquots of 5 μl are taken at regular intervals of time and the reaction is quenched by mixing with equal volume of 2X formamide stop mix. The samples are resolved on 20% denaturing polyacrylamide gels. The results are quantified and percentage of target RNA cleaved is plotted as a function of time.

Referring to FIG. 16, hammerhead ribozymes containing 6-methyl-uridine modification at U4 position cleave the target RNA efficiently.

Example 11: RNA cleavage activity of HHB ribozyme substituted with 6-methyl-Uridine Hammerhead ribozymes targeted to site B (see FIG. 17) were synthesized using solid-phase synthesis, as described above. U4 and U7 positions were modified with 6-methyl-uridine.

RNA cleavage reactions were carried out as described above. Referring to FIG. 18, hammerhead ribozymes containing 6-methyl-uridine modification at U4 and U7 positions cleave the target RNA efficiently.

Example 12: RNA cleavage activity of HHC ribozyme substituted with 6-methyl-Uridine Hammerhead ribozymes targeted to site C (see FIG. 19) were synthesized using solid-phase synthesis, as described above. U4 and U7 positions were modified with 6-methyl-uridine.

RNA cleavage reactions were carried out as described above. Referring to FIG. 20, hammerhead ribozymes containing 6-methyl-uridine modification at U4 positions cleave the target RNA efficiently.

Sequences listed in FIG. 7, 15, 17 19 and the modifications described in these figures are meant to be non-limiting examples. Those skilled in the art will recognize that variants (base-substitutions, deletions, insertions, mutations, chemical modifications) of the ribozyme and RNA containing other 2'-hydroxyl group modifications, including but not limited to amino acids, peptides and cholesterol, can be readily generated using techniques known in the art, and are within the scope of the present invention.

Example 13: Inhibition of Rat smooth muscle cell proliferation by 6-methyl-U substituted ribozyme HHA.

Hammerhead ribozyme (HHA) is targeted to a unique site (site A) within c-myb mRNA. Expression of c-myb protein has been shown to be essential for the proliferation of rat smooth muscle cell (Brown et al., 1992 *J. BioL Chem.* 267, 4625).

The ribozymes that cleaved site A within c-myb RNA described above were assayed for their effect on smooth muscle cell proliferation. Rat vascular smooth muscle cells were isolated and cultured as described (Stinchcomb et al., supra). HHA ribozymes were complexed with lipids and delivered into rat smooth muscle cells. Serum-starved cells were stimulated as described by Stinchcomb et al., supra. Briefly, serum-starved smooth muscle cells were washed twice with PBS, and the RNA/lipid complex was added. The plates were incubated for 4 hours at 37° C. The medium was then removed and DMEM containing 10% FBS, additives and 10 μM bromodeoxyuridine (BrdU) was added. In some wells, FBS was omitted to determine the baseline of unstimulated proliferation. The plates were incubated at 37° C. for 20–24 hours, fixed with 0.3% $H_2O_2$ in 100% methanol, and stained for BrdU incorporation by standard methods. In this procedure, cells that have proliferated and incorporated BrdU stain brown; non-proliferating cells are counter-stained a light purple. Both BrdU positive and BrdU negative cells were counted under the microscope. 300–600 total cells per well were counted. In the following experiments, the percentage of the total cells that have incorporated BrdU (% cell proliferation) is presented. Errors represent the range of duplicate wells. Percent inhibition then is calculated from the % cell proliferation values as follows: % inhibition=100 —100 (Ribozyme - 0% serum)/ (Control - 0% serum).

Referring to FIG. 21, active ribozymes substituted with 6-methyl-U at position 4 of HHA were successful in inhibiting rat smooth muscle cell proliferation. A catalytically inactive ribozyme (inactive HHA), which has two base substitutions within the core (these mutations inactivate a hammerhead ribozyme; Stinchcomb et al., supra), does not significantly inhibit rat smooth muscle cell proliferation.

Example 14: Inhibition of stromelysin production in human synovial fibroblast cells by 6-methyl-U substituted ribozyme HHC.

Hammerhead ribozyme (HHC) is targeted to a unique site (site C) with in stromelysin mRNA.

The general assay was as described (Draper et al., supra). Briefly, fibroblasts, which produce stromelysin, are serum-starved overnight and ribozymes or controls are offered to the cells the next day. Cells were maintained in serum-free media. The ribozyme were applied to the cells as free ribozyme, or in association with various delivery vehicles such as cationic lipids (including Transfectam™, Lipofectin™ and Lipofectamine™), conventional liposomes, non-phospholipid liposomes or biodegradable polymers. At the time of ribozyme addition, or up to 3 hours later, Interleukin-1α (typically 20 units/ml) can be added to the cells to induce a large increase in stromelysin expression. The production of stromelysin can then be monitored over a time course, usually up to 24 hours.

Supernatants were harvested 16 hours after IL-1 induction and assayed for stromelysin expression by ELISA. Polyclonal antibody against Matrix Metalloproteinase 3 (Biogenesis, NH) was used as the detecting antibody and anti-stromelysin monoclonal antibody was used as the capturing antibody in the sandwich ELISA (Maniatis et al., supra) to measure stromelysin expression.

Referring to FIG. 22, HHC ribozyme containing 6-methyl-U modification, caused a significant reduction in the level of stromelysin protein production. Catalytically inactive HHC had no significant effect on the protein level.

Other embodiments are within the following claims.

TABLE I

Characteristics of Ribozymes

Group I Introns

Size: ~200 to >1000 nucleotides.
Requires a U in the target sequence immediately 5' of the cleavage site.
Binds 4–6 nucleotides at 5' side of cleavage site.
Over 75 known members of this class. Found in *Tetrahymena thermophila* rRNA, fungal mitochondria, chloroplasts, phage T4, blue-green algae, and others.
RNAseP RNA (M1 RNA)

Size: ~290 to 400 nucleotides.
RNA portion of a ribonucleoprotein enzyme. Cleaves tRNA precursors to form mature tRNA.
Roughly 10 known members of this group all are bacterial in origin.
Hammerhead Ribozyme Size: ~13 to 40 nucleotides.
Requires the target sequence UH immediately 5' of the cleavage site.
Binds a variable number nucleotides on both sides of the cleavage site.
14 known members of this class. Found in a number of plant pathogens (virusoids) that use RNA as the infectious agent (FIG. 1)
Hairpin Ribozyme Size: ~50 nucleotides.
Requires the target sequence GUC immediately 3' of the cleavage site.

TABLE I-continued

Characteristics of Ribozymes

Figure 3:
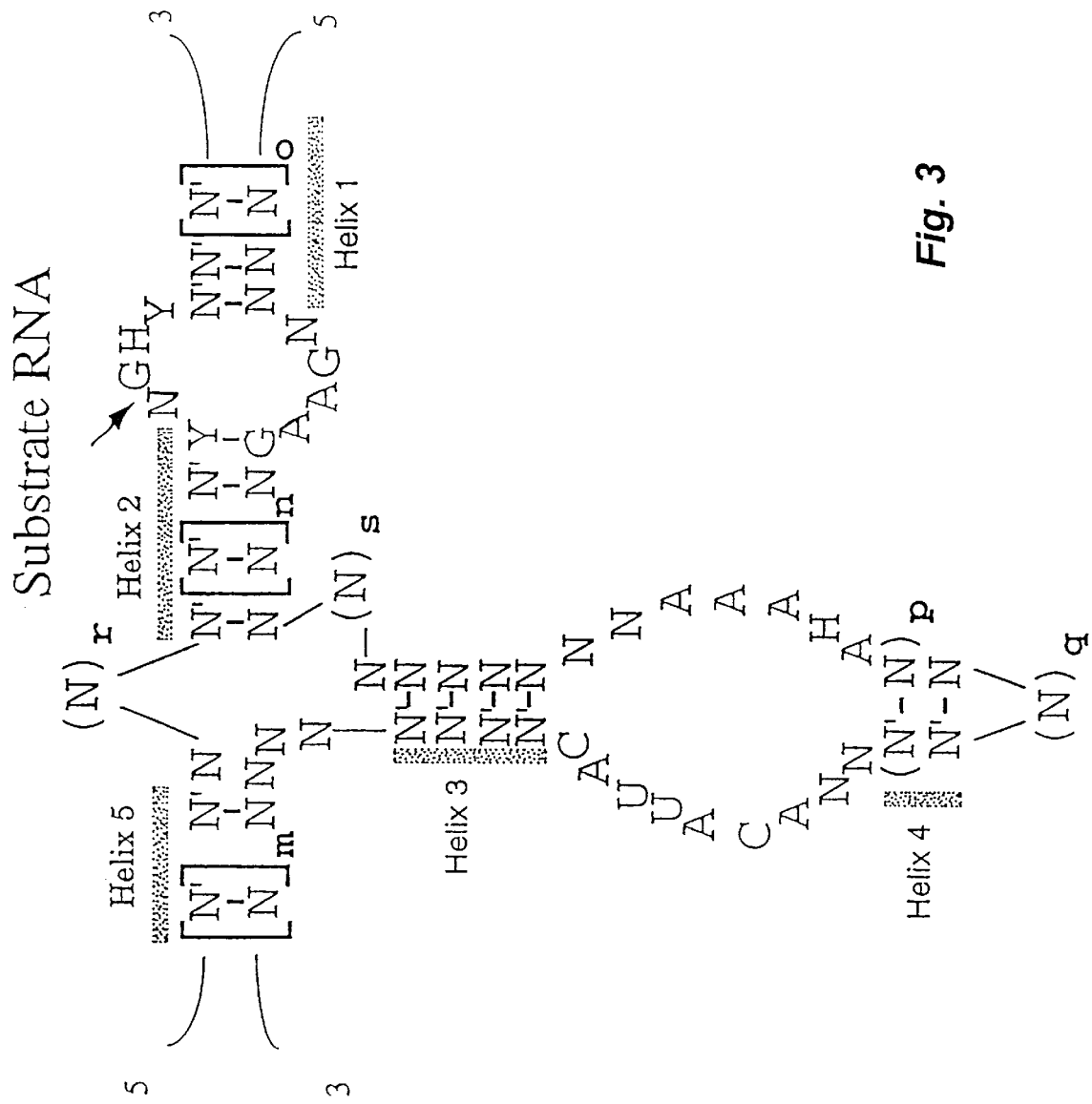
Figure 4:
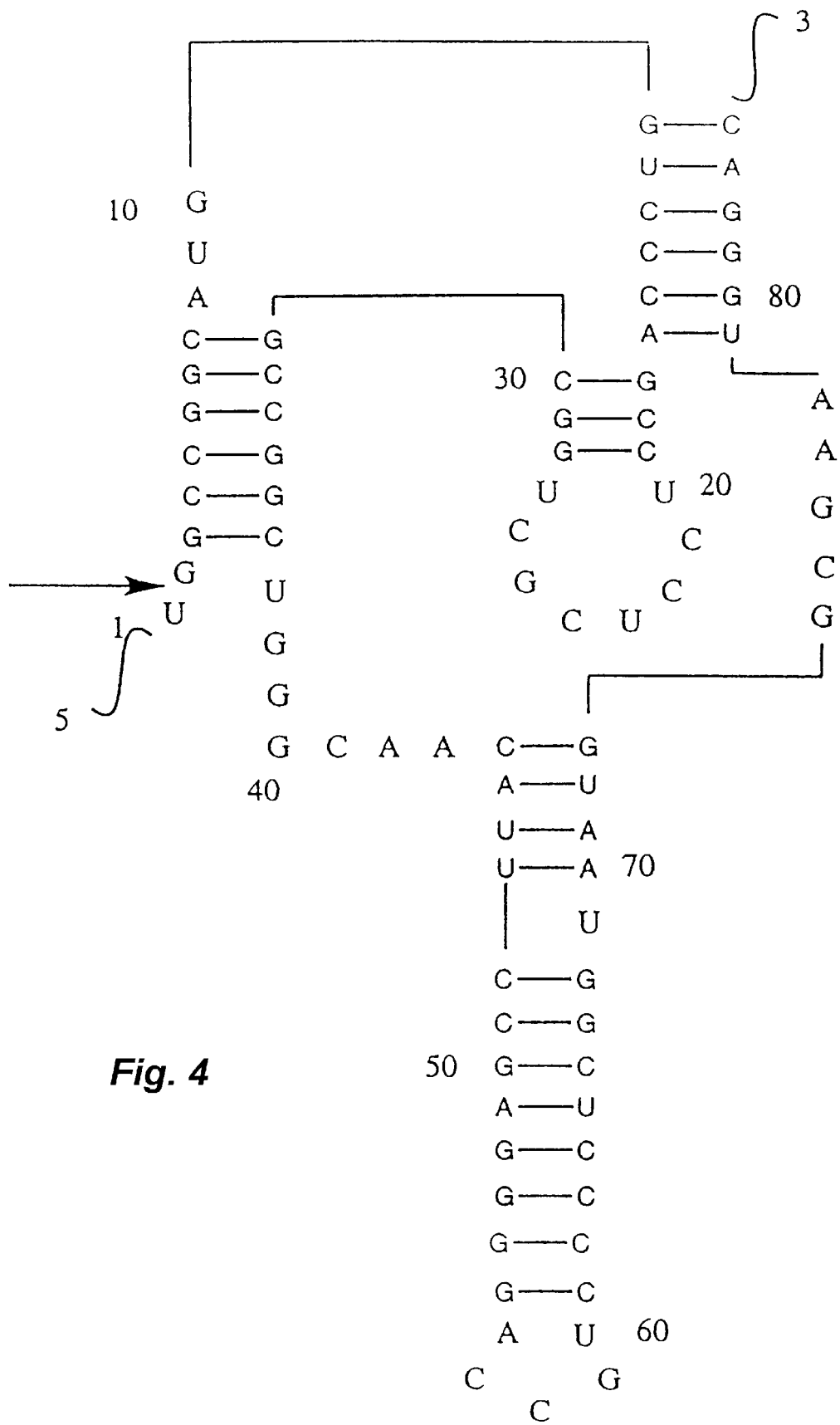
FIG. 4 is a representation of the general structure of the hepatitis delta virus ribozyme domain known in the art.

Binds 4–6 nucleotides at 5' side of the cleavage site and a variable number to the 3' side of the cleavage site.
Only 3 known member of this class. Found in three plant pathogen (satellite RNAs of the tobacco ringspot virus, arabis mosaic virus and chicory yellow mottle virus) which uses RNA as the infectious agent (FIG. 3).
Hepatitis Delta Virus (HDV) Ribozyme Size: 50–60 nucleotides (at present).
Cleavage of target RNAs recently demonstrated.
Sequence requirements not fully determined.
Binding sites and structural requirements not fully determined, although no sequences 5' of cleavage site are required.
Only 1 known member of this class. Found in human HDV (FIG. 4).
Neurospora VS RNA Ribozyme Size: ~144 nucleotides (at present)
Cleavage of target RNAs recently demonstrated.
Sequence requirements not fully determined.
Binding sites and structural requirements not fully determined. Only 1 known member of this class. Found in Neurospora VS RNA (FIG. 5).

What is claimed is:

1. An enzymatic nucleic acid molecule comprising at least one modified nucleotide base substitution, wherein said modified nucleotide base substitution enhances the enzymatic activity of said enzymatic nucleic acid molecule compared to an identical enzymatic nucleic acid molecule having an unmodified nucleotide base in place of said modified nucleotide base.

2. The enzymatic nucleic acid molecule of claim 1, wherein said enzymatic nucleic acid molecule is in a hammerhead motif.

3. The enzymatic nucleic acid molecule of claim 2, wherein said enzymatic nucleic acid molecule has a modified nucleotide base substitution at position 7.

4. The enzymatic nucleic acid molecule of claim 2, wherein said enzymatic nucleic acid molecule has at least one modified nucleotide base substitution in the loop II region of said enzymatic nucleic acid molecule.

5. The enzymatic nucleic acid molecule of claim 2, wherein said enzymatic nucleic acid molecule comprises a stem II region of length greater than or equal to two base-pairs.

6. The enzymatic nucleic acid molecule of claim 1, wherein said enzymatic nucleic acid molecule is in a hairpin motif.

7. An enzymatic nucleic acid molecule comprising at least two modified nucleotide base substitutions, wherein said modified nucleotide base substitution enhances the enzymatic activity of said enzymatic nucleic acid molecule compared to an identical enzymatic nucleic acid molecule having an unmodified nucleotide base in place of said modified nucleotide base.

8. A mammalian cell comprising the enzymatic nucleic acid molecule of claim 1 or 3.

9. The mammalian cell of claim 8, wherein said mammalian cell is a human cell.

* * * * *